(12) United States Patent
Richter et al.

(10) Patent No.: US 12,077,605 B2
(45) Date of Patent: *Sep. 3, 2024

(54) CYSTEINE PROTEASE INHIBITORS AND METHODS OF USE THEREOF

(71) Applicant: ANIXA BIOSCIENCES, INC., San Jose, CA (US)

(72) Inventors: Wolfgang Richter, Munich (DE); Muhammad Abbas, Lahore (PK); Lutz Weber, Stuttgart (DE); Amit Kumar, San Jose, CA (US)

(73) Assignee: Anixa Biosciences, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/157,293

(22) Filed: Jan. 20, 2023

(65) Prior Publication Data
US 2023/0234984 A1 Jul. 27, 2023

Related U.S. Application Data

(60) Provisional application No. 63/301,847, filed on Jan. 21, 2022.

(51) Int. Cl.
| | |
|---|---|
| *C07K 5/087* | (2006.01) |
| *A61K 31/245* | (2006.01) |
| *A61K 31/404* | (2006.01) |
| *A61K 31/427* | (2006.01) |
| *A61K 31/4418* | (2006.01) |
| *A61K 31/496* | (2006.01) |
| *A61K 31/4965* | (2006.01) |
| *A61K 31/513* | (2006.01) |
| *A61K 31/519* | (2006.01) |
| *A61K 31/635* | (2006.01) |
| *A61K 31/675* | (2006.01) |
| *A61K 31/7056* | (2006.01) |
| *A61K 31/7064* | (2006.01) |
| *A61K 31/7068* | (2006.01) |
| *A61K 31/7072* | (2006.01) |
| *A61K 31/7076* | (2006.01) |
| *A61K 36/746* | (2006.01) |
| *A61K 38/06* | (2006.01) |
| *A61P 31/14* | (2006.01) |

(52) U.S. Cl.
CPC .......... *C07K 5/0812* (2013.01); *A61K 31/245* (2013.01); *A61K 31/404* (2013.01); *A61K 31/427* (2013.01); *A61K 31/4418* (2013.01); *A61K 31/496* (2013.01); *A61K 31/4965* (2013.01); *A61K 31/513* (2013.01); *A61K 31/519* (2013.01); *A61K 31/635* (2013.01); *A61K 31/675* (2013.01); *A61K 31/7056* (2013.01); *A61K 31/7064* (2013.01); *A61K 31/7068* (2013.01); *A61K 31/7072* (2013.01); *A61K 31/7076* (2013.01); *A61K 36/746* (2013.01); *A61K 38/06* (2013.01); *A61P 31/14* (2018.01)

(58) Field of Classification Search
CPC .. C07K 5/0812; A61K 31/7064; A61K 38/06; A61K 31/4965; A61K 31/7076; A61K 31/675; A61K 31/7068; A61K 31/7072; A61K 31/7056; A61K 31/513; A61K 31/635; A61K 31/4418; A61K 31/519; A61K 31/404; A61K 31/245; A61K 31/427; A61K 31/496; A61K 36/746; A61P 31/14
See application file for complete search history.

(56) References Cited

U.S. PATENT DOCUMENTS

| 7,504,382 B2 | 3/2009 | Cai et al. |
|---|---|---|
| 9,474,759 B2 | 10/2016 | Chang et al. |
| 2006/0014821 A1 | 1/2006 | He et al. |

FOREIGN PATENT DOCUMENTS

| WO | WO-2004093860 A1 | 11/2004 | |
|---|---|---|---|
| WO | WO-2021252491 A1 * | 12/2021 | ........... A61K 31/404 |
| WO | WO-2022040186 A1 | 2/2022 | |

OTHER PUBLICATIONS

Berge, S.M., et al., "Pharmaceutical salts," J Pharm Sci 66(1):1-19, Elsevier B.V., United States (Jan. 1977).
International Search Report and Written Opinion for International Application No. PCT/US2021/046311, Commissioner for Patents, United States, mailed on Dec. 29, 2021, 8 pages.
Pajouhesh, H., and Lenz, G.R., "Medicinal chemical properties of successful central nervous system drugs," NeuroRx 2(4):541-553, Elsevier, Netherlands (Oct. 2005).
Sander, T., et al., "DataWarrior: an open-source program for chemistry aware data visualization and analysis," J Chem Inf Model 55(2):460-473, American Chemical Society, United States (Feb. 2015).
Sander, T., et al., "OSIRIS, an entirely in-house developed drug discovery informatics system," J Chem Inf Model 49(2):232-246, American Chemical Society, United States (Feb. 2009).
Zhang, L., et al., "Crystal structure of SARS-CoV-2 main protease provides a basis for design of improved α-ketoamide inhibitors," Science 368(6489):409-412, American Association for the Advancement of Science, United States (Apr. 2020).
Zhang, L., et al., "α-Ketoamides as Broad-Spectrum Inhibitors of Coronavirus and Enterovirus Replication: Structure-Based Design, Synthesis, and Activity Assessment," J Med Chem 63(9):4562-4578, American Chemical Society, United States (May 2020).

(Continued)

*Primary Examiner* — Li N Komatsu
(74) *Attorney, Agent, or Firm* — Sterne, Kessler, Goldstein & Fox P.L.L.C.

(57) ABSTRACT

Described herein are Mpro cysteine protease inhibitors and methods of utilizing such inhibitors in the treatment of diseases, disorders, or conditions. Also described herein are pharmaceutical compositions containing such compounds.

10 Claims, No Drawings

(56) References Cited

OTHER PUBLICATIONS

Thanigaimalai, P., et al., "Development of potent dipeptide-type SARS-CoV 3CL protease inhibitors with novel P3 scaffolds: design, synthesis, biological evaluation, and docking studies," Eur J Med Chem 68:372-384, Elsevier Masson s.r.l., France (Oct. 2013).
Tan, J., et al., "3C protease of enterovirus 68: structure-based design of Michael acceptor inhibitors and their broad-spectrum antiviral effects against picornaviruses," J Virol 87(8):4339-4351, American Society for Microbiology, United States (Apr. 2013).
Pubchem, SID 297435028, Pubchem.com, accessed at https://pubchem.ncbi.nlm.nih.gov/substance/297435028, accessed on May 1, 2024, 5 pages (Jan. 2016).

\* cited by examiner

CYSTEINE PROTEASE INHIBITORS AND METHODS OF USE THEREOF

CROSS REFERENCE TO RELATED APPLICATIONS

This application claims priority to U.S. Appl. No. 63/301,847 filed Jan. 21, 2022, the disclosure of which is hereby incorporated by reference herein in its entirety.

BACKGROUND

Coronaviruses infect humans and other animals, and cause a variety of highly prevalent and severe diseases, including severe acute respiratory syndrome (SARS), Middle East respiratory syndrome (MERS), and coronavirus disease 2019 (COVID-19). Main protease (Mpro) of SARS-CoV-2:Mpro is a key enzyme of coronaviruses and has a pivotal role in mediating viral replication and transcription. Small molecule inhibitors of SARS-CoV-2:Mpro provide an attractive drug target to treat or prevent these coronavirus and other viral infections.

BRIEF SUMMARY

In one aspect, provided herein are compounds of any one of Formulae I-XIV, see below, or a stereoisomer, tautomer, pharmaceutically acceptable salt, or solvate thereof, or a combination thereof, collectively referred to as "Compounds of the Disclosure" and individually referred to as a "Compound of the Disclosure." Compounds of the Disclosure are Mpro cysteine protease inhibitors that can be used to treat viral infections, e.g., COVID-19.

In another aspect, provided herein are pharmaceutical compositions comprising a Compound of the Disclosure and at least one pharmaceutically acceptable excipient.

In another aspect, provided herein are methods of treating or preventing a viral infection in an individual in need thereof, the method comprising administering to the individual a therapeutically effective amount of a Compound of the Disclosure, or a pharmaceutical composition thereof. In another aspect, the viral infection is caused by a virus in the Caliciviridae family, Picornaviridae family, or Coronaviridae family.

In another aspect, provided herein are methods of treating or preventing a viral infection in an individual in need thereof, the method comprising administering to the individual a therapeutically effective amount of a Compound of the Disclosure, or a pharmaceutical composition thereof, and a therapeutically effective amount of a viral polymerase inhibitor, a protease inhibitor, a fusion inhibitor, a serine protease inhibitor, or a CYP3A4 inhibitor, or a combination thereof. In another aspect, the viral polymerase inhibitor is Favipiravir, Bemnifosbuvir, AT-511, AT-527, Galidesivir, Remdesivir, Lufotrelvir, Molnupiravir, Sofosbuvir, or Ribavirin. In another aspect, the protease inhibitor is Lopinavir, Darunavir, or Atazanavir. In another aspect, the fusion inhibitor is Baricitinib or Umifenovir. In another aspect, the serine protease inhibitor is camostat mesylate. In another aspect, the CYP3A4 inhibitor is Ritonavir, Itraconazole or *Morinda citrifolia*.

In another aspect, provided herein is a Compound of the Disclosure, or a pharmaceutical composition thereof for use in treating or preventing a viral infection in an individual in need thereof.

In another aspect, provided herein is a Compound of the Disclosure, or a pharmaceutical composition thereof for use in treating or preventing a viral infection in an individual in need thereof, wherein the Compound of the Disclosure, or the pharmaceutical composition thereof, is to be administered with a therapeutically effective amount of a viral polymerase inhibitor, a protease inhibitor, a fusion inhibitor, a serine protease inhibitor, or a CYP3A4 inhibitor, or a combination thereof.

In another aspect, provided herein is the use of a Compound of the Disclosure, or a pharmaceutical composition thereof in the manufacture of a medicament for treating or preventing a viral infection in an individual in need thereof.

In another aspect, provided herein is the use of a Compound of the Disclosure, or a pharmaceutical composition thereof in the manufacture of a medicament for treating or preventing a viral infection in an individual in need thereof, wherein the Compound of the Disclosure, or the pharmaceutical composition thereof, is to be administered with a therapeutically effective amount of a viral polymerase inhibitor, a protease inhibitor, a fusion inhibitor, a serine protease inhibitor, or a CYP3A4 inhibitor, or a combination thereof.

In another aspect, provided herein is a method of treating or preventing a coronavirus infection in an individual in need thereof, comprising administering to the individual a therapeutically effective amount of a Compound of the Disclosure, or a pharmaceutical composition thereof. In another aspect, the coronavirus infection is severe acute respiratory syndrome coronavirus 2 (SARS-CoV-2).

In another aspect, provided herein are methods of treating or preventing a viral infection in an individual in need thereof, the method comprising administering to the individual a therapeutically effective amount of a Compound of Formula I' or II', or a pharmaceutical composition thereof, and a therapeutically effective amount of a viral polymerase inhibitor, a protease inhibitor, a fusion inhibitor, a serine protease inhibitor, or a CYP3A4 inhibitor, or a combination thereof. In another aspect, the viral infection is caused by a virus in the Caliciviridae family, Picornaviridae family, or Coronaviridae family. In another aspect, the viral polymerase inhibitor is Favipiravir, Bemnifosbuvir, AT-511, AT-527, Galidesivir, Remdesivir, Lufotrelvir, Molnupiravir, Sofosbuvir, or Ribavirin. In another aspect, the protease inhibitor is Lopinavir, Darunavir, or Atazanavir. In another aspect, the fusion inhibitor is Baricitinib or Umifenovir. In another aspect, the serine protease inhibitor is camostat mesylate. In another aspect, the CYP3A4 inhibitor is Ritonavir, Itraconazole or *Morinda citrifolia*.

In another aspect, provided herein is a Compound of Formula I' or II', or a pharmaceutical composition thereof for use in treating or preventing a viral infection in an individual in need thereof, wherein the Compound of the Disclosure, or the pharmaceutical composition thereof, is to be administered with a therapeutically effective amount of a viral polymerase inhibitor, a protease inhibitor, a fusion inhibitor, a serine protease inhibitor, or a CYP3A4 inhibitor, or a combination thereof.

In another aspect, provided herein is the use of a Compound of Formula I' or II', or a pharmaceutical composition thereof in the manufacture of a medicament for treating or preventing a viral infection in an individual in need thereof, wherein the Compound of the Disclosure, or the pharmaceutical composition thereof, is to be administered with a therapeutically effective amount of a viral polymerase inhibitor, a protease inhibitor, a fusion inhibitor, a serine protease inhibitor, or a CYP3A4 inhibitor, or a combination thereof.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

I. Definitions

In the context of this disclosure, a number of terms shall be utilized.

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry $4^{th}$ Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

An "alkyl" group refers to a straight or branched hydrocarbon chain radical consisting solely of carbon and hydrogen atoms, containing no unsaturation. In some embodiments, the "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the Compounds of the Disclosure may be designated as "$C_1$-$C_6$ alkyl" or similar designations. By way of example only, "$C_1$-$C_6$ alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, and hexyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a straight or branched hydrocarbon chain radical group consisting solely of carbon and hydrogen atoms, containing at least one carbon-carbon double bond. Non-limiting examples of an alkenyl group include —CH=$CH_2$, —C($CH_3$)=$CH_2$, —CH=$CHCH_3$, —CH=C($CH_3$)$_2$ and —C($CH_3$)=$CHCH_3$. In some embodiments, an alkenyl groups may have 2 to 6 carbons. Alkenyl groups can be substituted or unsubstituted. Depending on the structure, an alkenyl group can be a monoradical or a diradical (i.e., an alkenylene group).

The term "alkynyl" refers to a straight or branched hydrocarbon chain radical group consisting solely of carbon and hydrogen atoms, containing at least one carbon-carbon triple bond. Non-limiting examples of an alkynyl group include —C≡CH, —C≡$CCH_3$, —C≡$CCH_2CH_3$ and —C≡$CCH_2CH_2CH_3$. In some embodiments, an alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —NH$_2$ group.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

"Carboxy" refers to —CO$_2$H.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). In some embodiments, cycloalkyl groups include groups having from 3 to 10 ring atoms.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom.

A "heterocycloalkyl" group or "heteroalicyclic" group refers to a cycloalkyl group, wherein at least one skeletal ring atom is a heteroatom selected from nitrogen, oxygen and sulfur. The radicals may be fused with an aryl or heteroaryl or a cycloalkyl, e.g., to provide a bicyclic heterocycloalkyl group. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Non-limiting examples of heterocycloalkyl groups include:

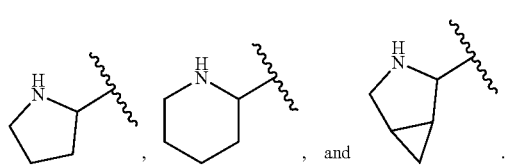

The term "halo" or, alternatively, "halogen" means fluoro, chloro, bromo and iodo.

The term "haloalkyl" refers to an alkyl group that is substituted with one or more halogens. The halogens may be the same or they may be different. Non-limiting examples of haloalkyls include —CH$_2$Cl, —CF$_3$, —CHF$_2$, —CH$_2$CF$_3$, —CF$_2$CF$_3$, and the like.

The terms "fluoroalkyl" and "fluoroalkoxy" include alkyl and alkoxy groups, respectively, that are substituted with one or more fluorine atoms. Non-limiting examples of fluoroalkyls include —CF$_3$, —CHF$_2$, —CH$_2$F, —CH$_2$CF$_3$, —CF$_2$CF$_3$, —CF$_2$CF$_2$CF$_3$, —CF(CH$_3$)$_3$, and the like. Non-limiting examples of fluoroalkoxy groups, include —OCF$_3$, —OCHF$_2$, —OCH$_2$F, —OCH$_2$CF$_3$, —OCF$_2$CF$_3$, —OCF$_2$CF$_2$CF$_3$, —OCF(CH$_3$)$_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH$_2$—NH—OCH$_3$, —CH$_2$—O—Si(CH$_3$)$_3$, —CH$_2$—CH=N—OCH$_3$, and —CH=CH—N(CH$_3$)—CH$_3$. In addition, up to two heteroatoms may be consecutive, such as, by way of example, —CH$_2$—NH—OCH$_3$ and —CH$_2$—O—Si(CH$_3$)$_3$. Excluding the number of heteroatoms, a "heteroalkyl" may have from 1 to 6 carbon atoms.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

"Optional" or "optionally" means that a subsequently described event or circumstance may or may not occur and that the description includes instances when the event or circumstance occurs and instances in which it does not.

The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, C$_1$-C$_6$ alkylalkyne, halo, acyl, acyloxy, —CO$_2$H, —CO$_2$-alkyl, nitro, haloalkyl, fluoroalkyl, and amino, including mono- and di-substituted amino groups (e.g. —NH$_2$, —NHR, —N(R)$_2$), and the protected derivatives thereof. By way of example, an optional substituents may be L$^s$R$^s$, wherein each L$^s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —(C$_1$-C$_6$ alkyl)-, or —(C$_2$-C$_6$ alkenyl)-; and each R$^s$ is independently selected from among H, (C$_1$-C$_6$ alkyl), (C$_3$-C$_5$ cycloalkyl), aryl, heteroaryl, heterocycloalkyl, and $C_1$-$C_6$ heteroalkyl. The protecting groups that may form the protective derivatives of the above substituents are found in sources such as Greene and Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure.

As used herein, the term "about" means within 10% of a given value or range. Thus, "about 10" means 9 to 11

The term a "therapeutically effective amount" as used herein refers to the amount of an Mpro cysteine protease inhibitor that, when administered to a mammal in need, is effective to at least partially ameliorate or to at least partially prevent conditions related to skin aging.

As used herein, the term "expression" includes the process by which polynucleotides are transcribed into mRNA and translated into peptides, polypeptides, or proteins.

The term "modulate" encompasses either a decrease or an increase in activity or expression depending on the target molecule.

The term "activator" is used in this specification to denote any molecular species that results in activation of the indicated receptor, regardless of whether the species itself binds to the receptor or a metabolite of the species binds to the receptor when the species is administered topically. Thus, the activator can be a ligand of the receptor or it can be an activator that is metabolized to the ligand of the receptor, i.e., a metabolite that is formed in tissue and is the actual ligand.

The term "individual", "patient", or "mammal" refers to a human, a non-human primate, canine, feline, bovine, ovine, porcine, murine, or other veterinary or laboratory mammal. Those skilled in the art recognize that a therapy which reduces the severity of a pathology in one species of mammal is predictive of the effect of the therapy on another species of mammal.

"Pharmaceutically acceptable salt" includes both acid and base addition salts. A pharmaceutically acceptable salt of any one of the Compounds of the Disclosure is intended to encompass any and all pharmaceutically suitable salt forms. Preferred pharmaceutically acceptable salts of the Compounds of the Disclosure are pharmaceutically acceptable acid addition salts, and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

As used herein, "treatment" or "treating" or "palliating" or "ameliorating" are used interchangeably herein. These terms refer to an approach for obtaining beneficial or desired results including but not limited to therapeutic benefit. By "therapeutic benefit" is meant eradication or amelioration of the underlying disease, disorder, and/or condition, e.g., an infection, being treated. Also, a therapeutic benefit is achieved with the eradication or amelioration of one or more of the physiological symptoms associated with the underlying disease, disorder, and/or condition, such that an improvement is observed in the patient, notwithstanding that the patient is still afflicted with the underlying disorder.

As used herein, the terms "prevent" and "preventing" refer to partially or completely delaying onset of a disease, disorder, and/or condition, e.g., an infection; partially or completely delaying onset of one or more signs, symptoms, features, or manifestations (e.g., clinical or physiological signs, symptoms, features, or manifestations) of a disease, disorder, and/or condition; partially or completely delaying progression from a disease, disorder, and/or condition; and/ or decreasing the risk of developing a pathology associated with the disease, disorder, and/or condition. For prophylactic benefit, the compositions may be administered to a patient at risk of developing a particular disease, or to a patient reporting one or more of the physiological symptoms of a disease, even though a diagnosis of this disease has not been made.

II. Mpro Cysteine Protease Inhibitors

The virus SARS-CoV-2 is a virus from the corona virus family. Coronaviruses (CoV) are a large family of viruses that cause illness ranging from the common cold to more severe diseases. These viruses all share a cysteine proteinase "main protease"—Mpro that is a key enzyme of coronaviruses and has a pivotal role in mediating viral replication and transcription, making it an attractive drug target for SARS-CoV-2.

Mpro processes polyproteins that are translated from the viral RNA once the virus has entered human cells (Hilgenfeld et al. "Crystal structure of SARS-CoV-2 main protease provides a basis for design of improved α-ketoamide inhibitors", Science 24 Vol. 368, Issue 6489, pp. 409-412). The crystal structure of the enzyme Mpro was identified at a resolution of 1.75 Angstroms showing an alpha-ketoamide type inhibitor in its active site.

Compounds of the Disclosure are Mpro cysteine protease inhibitors. These compounds and compositions comprising these compounds, are thus useful for the treatment of viral infections, e.g., caused by a virus in the Caliciviridae family, Picornaviridae family, or Coronaviridae family, e.g., caused by a coronavirus infection including, but not limited to, COVID-19.

In one aspect, the disclosure provides a compound of Formula I:

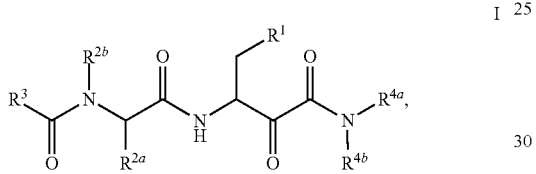

or a stereoisomer, tautomer, pharmaceutically acceptable salt, or solvate thereof, wherein:

$R^1$ is selected from the group consisting of:

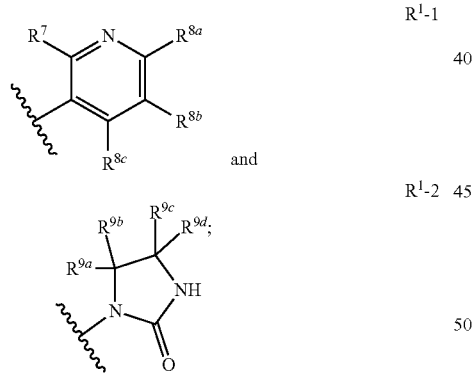

$R^{2a}$ is selected from the group consisting of $C_{1-6}$ alkyl, $C_{2-6}$ alkenyl, $C_{3-6}$ cycloalkyl, and —$C_{1-6}$ alkyl-$C_{3-6}$ cycloalkyl, wherein the $C_{1-6}$ alkyl, $C_{2-6}$ alkenyl, $C_{3-6}$ cycloalkyl, or —$C_{1-6}$ alkyl-$C_{3-6}$ cycloalkyl is independently optionally substituted with one, two, three, or four groups independently selected from the group consisting of halogen, $C_{1-6}$ alkyl, $C_{1-6}$ haloalkyl, —$OR^5$, and —$N(R^5)(R^6)$;

$R^{2b}$ is selected from the group consisting of hydrogen and $C_{1-6}$ alkyl; or $R^{2a}$ and $R^{2b}$ taken together form a 5-, 6-, 7-, or 8-membered heterocycloalkyl, wherein the 5-, 6-, 7-, or 8-membered heterocycloalkyl is independently optionally substituted with one, two, three, or four groups independently selected from the group consisting of halogen, $C_{1-6}$ alkyl, $C_{1-6}$ haloalkyl, —$OR^5$, and —$N(R^5)(R^6)$;

$R^3$ is selected from the group consisting of:

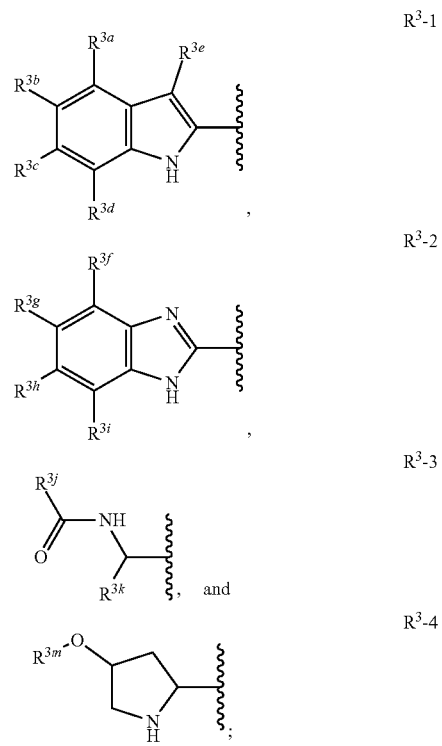

$R^{3a}$, $R^{3b}$, $R^{3c}$ and $R^{3d}$ are independently selected from the group consisting of hydrogen, halogen, cyano, $C_{1-6}$ alkyl, $C_{1-6}$ haloalkyl, $C_{3-6}$ cycloalkyl, —$OR^5$, and —$N(R^5)(R^6)$; or $R^{3a}$ and $R^{3b}$ taken together with the carbon atoms to which they are attached form a 5- or 6-membered heterocycloalkyl, wherein the 5- or 6-membered heterocycloalkyl is independently optionally substituted with one or two $C_{1-6}$ alkyl groups; and $R^{3c}$ and $R^{3d}$ are independently selected from the group consisting of hydrogen, halogen, cyano, $C_{1-6}$ alkyl, $C_{1-6}$ haloalkyl, $C_{3-6}$ cycloalkyl, —$OR^5$, and —$N(R^5)(R^6)$; or $R^{3b}$ and $R^{3c}$ taken together with the carbon atoms to which they are attached form a 5- or 6-membered heterocycloalkyl, wherein the 5- or 6-membered heterocycloalkyl is independently optionally substituted with one or two $C_{1-6}$ alkyl groups; and $R^{3a}$ and $R^{3d}$ are independently selected from the group consisting of hydrogen, halogen, cyano, $C_{1-6}$ alkyl, $C_{1-6}$ haloalkyl, $C_{3-6}$ cycloalkyl, —$OR^5$, and —$N(R^5)(R^6)$; or $R^{3c}$ and $R^{3d}$ taken together with the carbon atoms to which they are attached form a 5- or 6-membered heterocycloalkyl, wherein the 5- or 6-membered heterocycloalkyl is independently optionally substituted with one or two $C_{1-6}$ alkyl groups; and $R^{3a}$ and $R^{3b}$ are independently selected from the group consisting of hydrogen, halogen, cyano, $C_{1-6}$ alkyl, $C_{1-6}$ haloalkyl, $C_{3-6}$ cycloalkyl, —$OR^5$, and —$N(R^5)(R^6)$;

$R^{3e}$ is selected from the group consisting of hydrogen and $C_{1-6}$ alkyl;

$R^{3f}$, $R^{3g}$, $R^{3h}$, and $R^{3i}$ are independently selected from the group consisting of hydrogen, halogen, cyano, $C_{1-6}$ alkyl, $C_{1-6}$ haloalkyl, $C_{3-6}$ cycloalkyl, —$OR^5$, and —$N(R^5)(R^6)$; or $R^{3f}$ and $R^{3g}$ taken together with the carbon atoms to which they are attached form a 5- or 6-membered heterocycloalkyl, wherein the 5- or 6-membered heterocycloalkyl is independently optionally substituted with one or two $C_{1-6}$ alkyl groups; and $R^{3h}$ and $R^{3i}$ are independently selected from the group consisting of hydrogen, halogen, cyano, $C_{1-6}$ alkyl, $C_{1-6}$ haloalkyl, $C_{3-6}$ cycloalkyl, —$OR^5$, and —$N(R^5)(R^6)$; or $R^{3g}$ and $R^{3h}$ taken together with the carbon atoms to which they are attached form a 5- or 6-membered heterocycloalkyl, wherein the 5- or 6-membered heterocycloalkyl is independently optionally substituted with one or two $C_{1-6}$ alkyl groups; and $R^{3f}$ and $R^{3i}$ are independently selected from the group consisting of hydrogen, halogen, cyano, $C_{1-6}$ alkyl, $C_{1-6}$ haloalkyl, $C_{3-6}$ cycloalkyl, —$OR^5$, and —$N(R^5)(R^6)$; or $R^{3h}$ and $R^{3i}$ taken together with the carbon atoms to which they are attached form a 5- or 6-membered heterocycloalkyl, wherein the 5- or 6-membered heterocycloalkyl is independently optionally substituted with one or two $C_{1-6}$ alkyl groups; and $R^{3f}$ and $R^{3g}$ are independently selected from the group consisting of hydrogen, halogen, cyano, $C_{1-6}$ alkyl, $C_{1-6}$ haloalkyl, $C_{3-6}$ cycloalkyl, —$OR^5$, and —$N(R^5)(R^6)$;

$R^{3j}$ is selected from the group consisting of $C_{1-6}$ alkyl and $C_{1-6}$ haloalkyl;

$R^{3k}$ is selected from the group consisting of $C_{1-6}$ alkyl and $C_{3-6}$ cycloalkyl;

$R^{3m}$ is selected from the group consisting of hydrogen and $C_{1-6}$ alkyl;

$R^{4a}$ is $C_{1-3}$ alkyl;

$R^{4b}$ is selected from the group consisting of hydrogen and $C_{1-3}$ alkyl; or $R^{4a}$ and $R^{4b}$ taken together with the nitrogen to which they are attached form a 3- to 8-membered heterocycloalkyl;

each $R^5$ is independently selected from the group consisting of hydrogen, $C_{1-6}$ alkyl, $C_{1-6}$ haloalkyl, $C_{2-6}$ alkenyl, $C_{2-6}$ alkynyl, $C_{3-6}$ cycloalkyl, $C_{2-9}$ heterocycloalkyl, $C_{6-10}$ aryl, and $C_{1-9}$ heteroaryl, wherein the $C_{1-6}$ alkyl, $C_{2-6}$ alkenyl, $C_{2-6}$ alkynyl, $C_{3-6}$ cycloalkyl, $C_{2-9}$ heterocycloalkyl, $C_{6-10}$ aryl, or $C_{1-9}$ heteroaryl are independently optionally substituted with one, two, or three groups independently selected from the group consisting of halogen, $C_{1-6}$ alkyl, $C_{1-6}$ haloalkyl, $C_{1-6}$ alkoxy, $C_{3-6}$ cycloalkyl, $C_{2-9}$ heterocycloalkyl, $C_{6-10}$ aryl, and $C_{1-9}$ heteroaryl;

each $R^6$ is independently selected from the group consisting of hydrogen, $C_{1-6}$ alkyl, and $C_{1-6}$ haloalkyl;

$R^7$ is selected from the group consisting of —$OR^{7a}$ and —$NR^{7b}R^{7c}$;

$R^{7a}$ is selected from the group consisting of hydrogen, $C_{1-6}$ alkyl, and $C_{3-6}$ cycloalkyl;

$R^{7b}$ and $R^{7c}$ are independently selected from the group consisting of hydrogen, $C_{1-6}$ alkyl, and $C_{3-6}$ cycloalkyl;

$R^{8a}$, $R^{8b}$, and $R^{8c}$ are independently selected from the group consisting of hydrogen, halogen, $C_{1-6}$ alkyl, $C_{1-6}$ haloalkyl, and —$N(R^5)(R^6)$; and $R^{9a}$, $R^{9b}$, $R^{9c}$, and $R^{9d}$ are independently selected from the group consisting of hydrogen, halogen, $C_{1-6}$ alkyl, $C_{1-6}$ haloalkyl, —$OR^5$, and —$N(R^5)(R^6)$.

In another aspect, the disclosure provides a compound of Formula I, or a stereoisomer, tautomer, pharmaceutically acceptable salt, or solvate thereof, wherein:

$R^{2a}$ is selected from the group consisting of $C_{1-6}$ alkyl, $C_{2-6}$ alkenyl, $C_{3-6}$ cycloalkyl, and —$C_{1-6}$ alkyl-$C_{3-6}$ cycloalkyl, wherein the $C_{1-6}$ alkyl, $C_{2-6}$ alkenyl, $C_{3-6}$ cycloalkyl, or —$C_{1-6}$ alkyl-$C_{3-6}$ cycloalkyl is independently optionally substituted with one, two, three, or four groups independently selected from the group consisting of halogen, $C_{1-6}$ alkyl, $C_{1-6}$ haloalkyl, —$OR^5$, and —$N(R^5)(R^6)$; and $R^{2b}$ is selected from the group consisting of hydrogen and $C_{1-6}$ alkyl.

In another aspect, the disclosure provides a compound of Formula I, or a stereoisomer, tautomer, pharmaceutically acceptable salt, or solvate thereof, wherein:

$R^{2a}$ is selected from the group consisting of $C_{1-6}$ alkyl, $C_{2-6}$ alkenyl, $C_{3-6}$ cycloalkyl, and —$C_{1-6}$ alkyl-$C_{3-6}$ cycloalkyl, wherein the $C_{1-6}$ alkyl, $C_{2-6}$ alkenyl, $C_{3-6}$ cycloalkyl, or —$C_{1-6}$ alkyl-$C_{3-6}$ cycloalkyl is independently optionally substituted with one, two, three, or four groups independently selected from the group consisting of halogen, $C_{1-6}$ alkyl, $C_{1-6}$ haloalkyl, —$OR^5$, and —$N(R^5)(R^6)$; and $R^{2b}$ is hydrogen.

In another aspect, the disclosure provides a compound of Formula I, or a stereoisomer, tautomer, pharmaceutically acceptable salt, or solvate thereof, wherein $R^{2a}$ and $R^{2b}$ taken together form a 5-, 6-, 7-, or 8-membered heterocycloalkyl, wherein the 5-, 6-, 7-, or 8-membered heterocycloalkyl is independently optionally substituted with one, two, three, or four $C_{1-6}$ alkyl groups.

In another aspect, the disclosure provides a compound of Formula II:

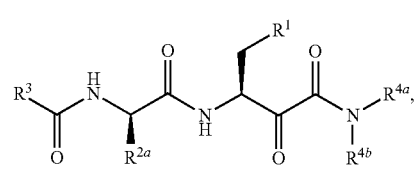

or a stereoisomer, tautomer, pharmaceutically acceptable salt, or solvate thereof, wherein $R^1$, $R^{2a}$, $R^3$, $R^{4a}$, and $R^{4b}$ are as defined in connection with Formula I.

In another aspect, the disclosure provides a compound of Formula III:

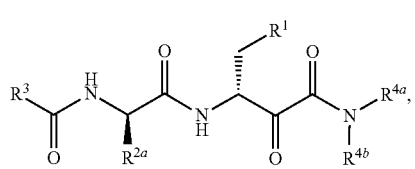

or a stereoisomer, tautomer, pharmaceutically acceptable salt, or solvate thereof, wherein $R^1$, $R^{2a}$, $R^3$, $R^{4a}$, and $R^{4b}$ are as defined in connection with Formula I.

In another aspect, the disclosure provides a compound of Formula IV:

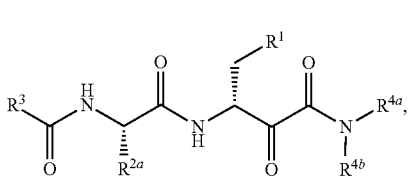

IV or a stereoisomer, tautomer, pharmaceutically acceptable salt, or solvate thereof, wherein $R^1$, $R^{2a}$, $R^3$, $R^{4a}$, and $R^{4b}$ are as defined in connection with Formula I.

In another aspect, the disclosure provides a compound of Formula V:

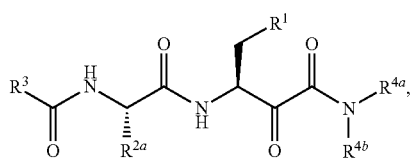

V or a stereoisomer, tautomer, pharmaceutically acceptable salt or solvate thereof, wherein $R^1$, $R^{2a}$, $R^3$, $R^{4a}$, and $R^{4b}$ are as defined in connection with Formula I.

In another aspect, the disclosure provides a compound of Formula VI:

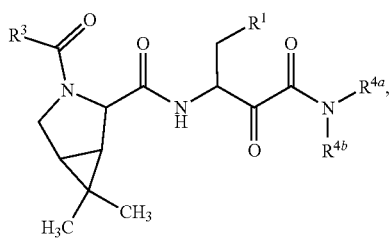

VI or a stereoisomer, tautomer, pharmaceutically acceptable salt or solvate thereof, wherein $R^1$, $R^3$, $R^{4a}$, and $R^{4b}$ are as defined in connection with Formula I.

In another aspect, the disclosure provides a compound of Formula VII:

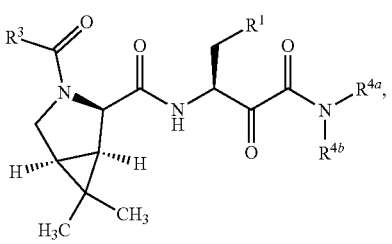

VII or a stereoisomer, tautomer, pharmaceutically acceptable salt or solvate thereof, wherein $R^1$, $R^3$, $R^{4a}$, and $R^{4b}$ are as defined in connection with Formula I.

In another aspect, the disclosure provides a compound of Formula VIII:

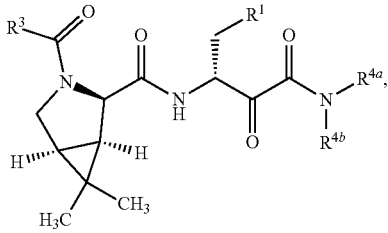

VIII or a stereoisomer, tautomer, pharmaceutically acceptable salt or solvate thereof, wherein $R^1$, $R^3$, $R^{4a}$, and $R^{4b}$ are as defined in connection with Formula I.

In another aspect, the disclosure provides a compound of Formula IX:

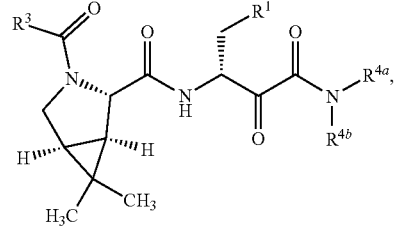

IX or a stereoisomer, tautomer, pharmaceutically acceptable salt or solvate thereof, wherein $R^1$, $R^3$, $R^{4a}$, and $R^{4b}$ are as defined in connection with Formula I.

In another aspect, the disclosure provides a compound of Formula X:

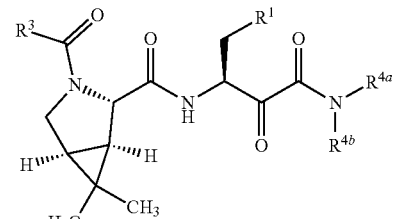

X or a stereoisomer, tautomer, pharmaceutically acceptable salt or solvate thereof, wherein $R^1$, $R^3$, $R^{4a}$, and $R^{4b}$ are as defined in connection with Formula I.

In another aspect, the disclosure provides a compound of Formula XI:

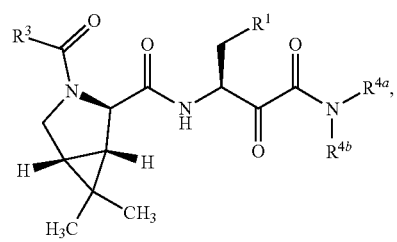

XI or a stereoisomer, tautomer, pharmaceutically acceptable salt or solvate thereof, wherein $R^1$, $R^3$, $R^{4a}$, and $R^{4b}$ are as defined in connection with Formula I.

In another aspect, the disclosure provides a compound of Formula XII:

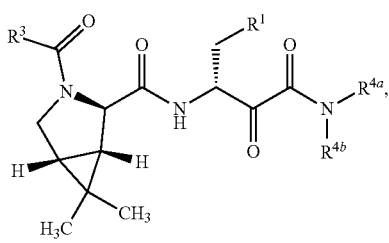

or a stereoisomer, tautomer, pharmaceutically acceptable salt or solvate thereof, wherein $R^1$, $R^3$, $R^{4a}$, and $R^{4b}$ are as defined in connection with Formula I.

In another aspect, the disclosure provides a compound of Formula XIII:

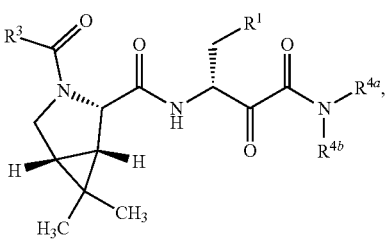

or a stereoisomer, tautomer, pharmaceutically acceptable salt or solvate thereof, wherein $R^1$, $R^3$, $R^{4a}$, and $R^{4b}$ are as defined in connection with Formula I.

In another aspect, the disclosure provides a compound of Formula XIV:

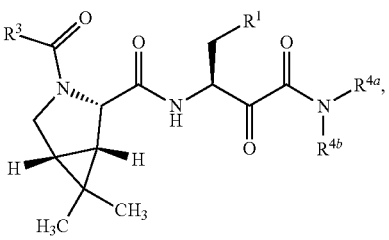

or a stereoisomer, tautomer, pharmaceutically acceptable salt or solvate thereof, wherein $R^1$, $R^3$, $R^{4a}$, and $R^{4b}$ are as defined in connection with Formula I.

In another aspect, the disclosure provides a compound of any one of Formulae I-XIV, or a stereoisomer, tautomer, pharmaceutically acceptable salt, or solvate thereof, wherein $R^1$ is $R^1$-1. In another aspect, $R^{8a}$, $R^{8b}$, and $R^{8c}$ are hydrogen. In another aspect, $R^7$ is $-OR^{7a}$. In another aspect, $R^{7a}$ is hydrogen. In another aspect, $R^{7a}$ is $C_{1-3}$ alkyl. In another aspect, $R^7$ is $-NR^{7b}R^{7c}$. In another aspect, $R^{7b}$ and $R^{7c}$ are hydrogen. In another aspect, $R^{7b}$ is $C_{1-3}$ alkyl and $R^{7c}$ is hydrogen.

In another aspect, the disclosure provides a compound of any one of Formulae I-XIV, or a stereoisomer, tautomer, pharmaceutically acceptable salt, or solvate thereof, wherein $R^1$ is $R^1$-2. In another aspect, $R^{9a}$, $R^{9b}$, $R^{9c}$, and $R^{9d}$ are hydrogen.

In another aspect, the disclosure provides a compound of any one of Formulae I-V, or a stereoisomer, tautomer, pharmaceutically acceptable salt, or solvate thereof, wherein $R^{2a}$ is $C_{1-6}$ alkyl.

In another aspect, the disclosure provides a compound of any one of Formulae I-V, or a stereoisomer, tautomer, pharmaceutically acceptable salt, or solvate thereof, wherein $R^{2a}$ is $-C_{1-6}$ alkyl-$C_{3-6}$ cycloalkyl.

In another aspect, the disclosure provides a compound of any one of Formulae I-V, or a stereoisomer, tautomer, pharmaceutically acceptable salt, or solvate thereof, wherein $R^{2a}$ is $-CH_2CH(CH_3)_2$.

In another aspect, the disclosure provides a compound of any one of Formulae I-XIV, or a stereoisomer, tautomer, pharmaceutically acceptable salt, or solvate thereof, wherein $R^3$ is $R^3$-1. In another aspect, $R^3$-1 is selected from the group consisting of:

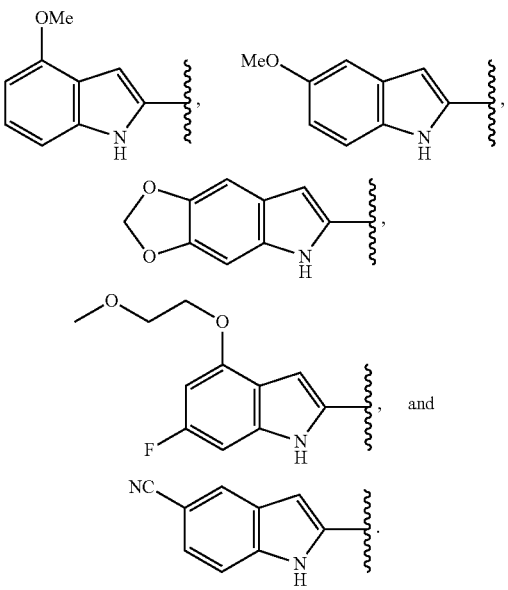

In another aspect, the disclosure provides a compound of any one of Formulae I-XIV, or a stereoisomer, tautomer, pharmaceutically acceptable salt, or solvate thereof, wherein $R^3$ is $R^3$-2. In another aspect, $R^3$-2 is selected from the group consisting of:

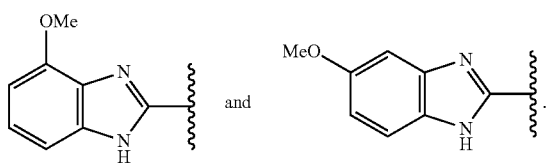 [SMILES: *c1nc2c(OC)cccc2[nH]1 ; *c1nc2cc(OC)ccc2[nH]1]

In another aspect, the disclosure provides a compound of any one of Formulae I-XIV, or a stereoisomer, tautomer, pharmaceutically acceptable salt, or solvate thereof, wherein $R^3$ is $R^3$-3. In another aspect, $R^3$-3 is:

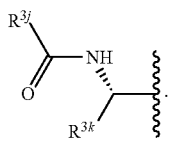

In another aspect, $R^{3j}$ is $C_{1-3}$haloalkyl. In another aspect, $R^{3j}$ is —$CF_3$. In another aspect, $R^{3k}$ is $C_{1-6}$ alkyl. In another aspect, $R^{3k}$ is —$C(CH_3)_3$.

In another aspect, the disclosure provides a compound of any one of Formulae I-XIV, or a stereoisomer, tautomer, pharmaceutically acceptable salt, or solvate thereof, wherein $R^3$ is $R^3$-4. In another aspect, $R^3$-4 is:

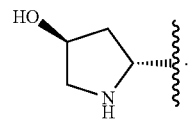

In another aspect, the disclosure provides a compound of any one of Formulae I-XIV, or a stereoisomer, tautomer, pharmaceutically acceptable salt, or solvate thereof, wherein $R^{4b}$ is hydrogen. In another aspect, $R^{4a}$ is —$CH_3$.

In another aspect, the disclosure provides a compound of any one of Formulae I-XIV, or a stereoisomer, tautomer, pharmaceutically acceptable salt, or solvate thereof, wherein $R^{4a}$ and $R^{4b}$ taken together with the nitrogen to which they are attached form a 3- to 8-membered heterocycloalkyl.

In another aspect, the disclosure provides a compound of Table 1, or a stereoisomer, tautomer, pharmaceutically acceptable salt, or solvate thereof.

TABLE 1

| Cmpd. No. | Structure | Name |
|---|---|---|
| 1 | 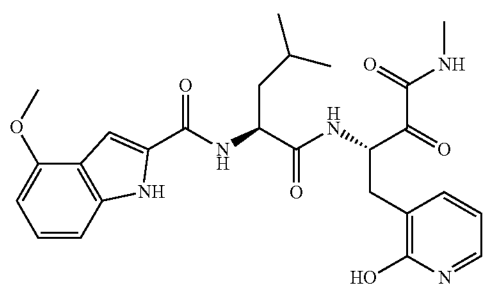 [SMILES: CNC(=O)C(=O)[C@H](Cc1cccnc1O)NC(=O)[C@H](CC(C)C)NC(=O)c1cc2c(OC)cccc2[nH]1] | N-((S)-1-(((S)-1-(2-hydroxypyridin-3-yl)-4-(methylamino)-3,4-dioxobutan-2-yl)amino)-4-methyl-1-oxopentan-2-yl)-4-methoxy-1H-indole-2-carboxamide |
| 2 | 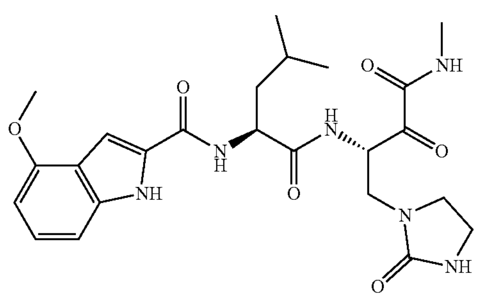 [SMILES: CNC(=O)C(=O)[C@H](CN1CCNC1=O)NC(=O)[C@H](CC(C)C)NC(=O)c1cc2c(OC)cccc2[nH]1] | 4-methoxy-N-((S)-4-methyl-1-(((S)-4-(methylamino)-3,4-dioxo-1-(2-oxoimidazolidin-1-yl)butan-2-yl)amino)-1-oxopentan-2-yl)-1H-indole-2-carboxamide |
| 3 | 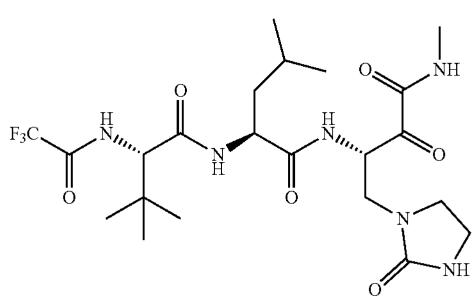 [SMILES: CNC(=O)C(=O)[C@H](CN1CCNC1=O)NC(=O)[C@H](CC(C)C)NC(=O)[C@@H](NC(=O)C(F)(F)F)C(C)(C)C] | (S)-2-((S)-3,3-dimethyl-2-(2,2,2-trifluoroacetamido)butanamido)-4-methyl-N-((S)-4-(methylamino)-3,4-dioxo-1-(2-oxoimidazolidin-1-yl)butan-2-yl)pentanamide |

TABLE 1-continued

| Cmpd. No. | Structure | Name |
|---|---|---|
| 4 | 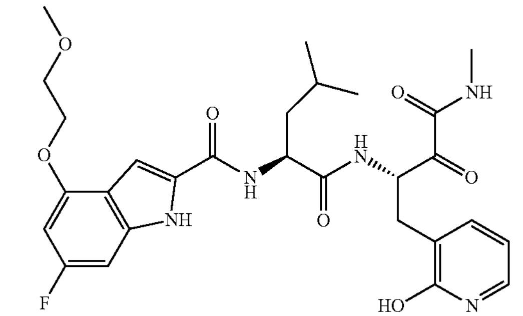 [SMILES: CNC(=O)C(=O)[C@H](Cc1cccnc1O)NC(=O)[C@H](CC(C)C)NC(=O)c1cc2c(OCCOC)cc(F)cc2[nH]1] | 6-fluoro-N-((S)-1-(((S)-1-(2-hydroxypyridin-3-yl)-4-(methylamino)-3,4-dioxobutan-2-yl)amino)-4-methyl-1-oxopentan-2-yl)-4-(2-methoxyethoxy)-1H-indole-2-carboxamide |
| 5 | 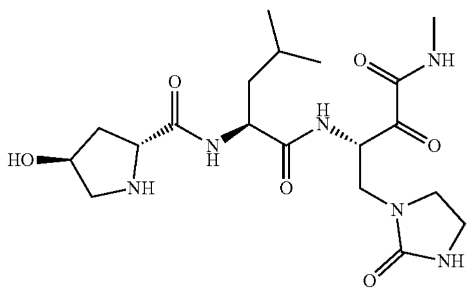 [SMILES: CNC(=O)C(=O)[C@H](CN1CCNC1=O)NC(=O)[C@H](CC(C)C)NC(=O)[C@H]1C[C@H](O)CN1] | (2R,4S)-4-hydroxy-N-((S)-4-methyl-1-(((S)-4-(methylamino)-3,4-dioxo-1-(2-oxoimidazolidin-1-yl)butan-2-yl)amino)-1-oxopentan-2-yl)pyrrolidine-2-carboxamide |
| 6 | 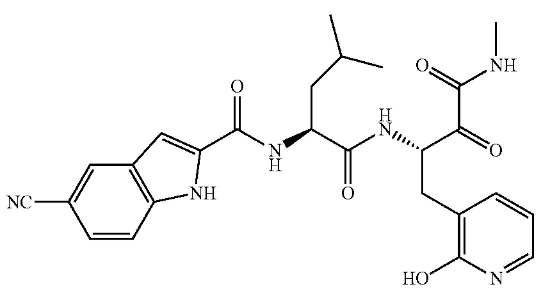 [SMILES: CNC(=O)C(=O)[C@H](Cc1cccnc1O)NC(=O)[C@H](CC(C)C)NC(=O)c1cc2cc(C#N)ccc2[nH]1] | 5-cyano-N-((S)-1-(2-hydroxypyridin-3-yl)-4-(methylamino)-3,4-dioxobutan-2-yl)amino)-4-methyl-1-oxopentan-2-yl)-1H-indole-2-carboxamide |
| 7 | 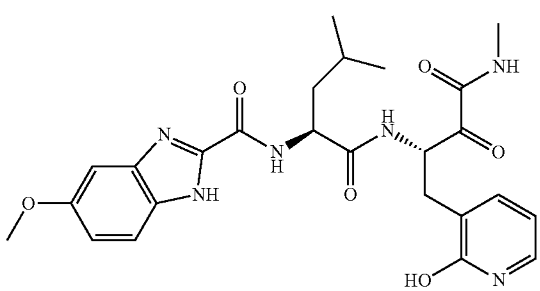 [SMILES: CNC(=O)C(=O)[C@H](Cc1cccnc1O)NC(=O)[C@H](CC(C)C)NC(=O)c1nc2cc(OC)ccc2[nH]1] | N-((S)-1-(((S)-1-(2-hydroxypyridin-3-yl)-4-(methylamino)-3,4-dioxobutan-2-yl)amino)-4-methyl-1-oxopentan-2-yl)-5-methoxy-1H-benzo[d]imidazole-2-carboxamide |
| 8 | 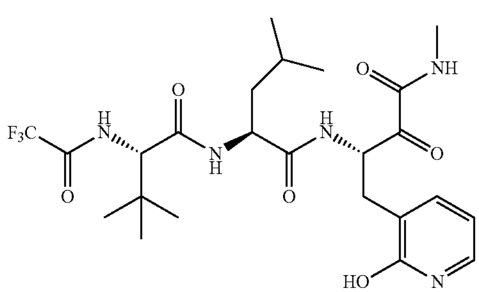 [SMILES: CNC(=O)C(=O)[C@H](Cc1cccnc1O)NC(=O)[C@H](CC(C)C)NC(=O)[C@@H](NC(=O)C(F)(F)F)C(C)(C)C] | (S)-2-((S)-3,3-dimethyl-2-(2,2,2-trifluoroacetamido)butanamido)-N-((S)-1-(2-hydroxypyridin-3-yl)-4-(methylamino)-3,4-dioxobutan-2-yl)-4-methylpentanamide |

TABLE 1-continued

| Cmpd. No. | Structure | Name |
|---|---|---|
| 9 | 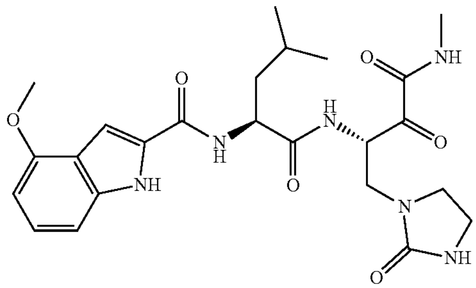 [SMILES: CNC(=O)C(=O)[C@H](CN1CCNC1=O)NC(=O)[C@H](CC(C)C)NC(=O)c1cc2c(OC)cccc2[nH]1] | 4-methoxy-N-((S)-methyl-2-(((S)-4-(methylamino)-3,4-dioxo-1-(2-oxoimidazolidin-1-yl)butan-2-yl)amino)-1-oxopentan-2-yl)-1H-benzo[d]imidazole-2-carboxamide |
| 10 | 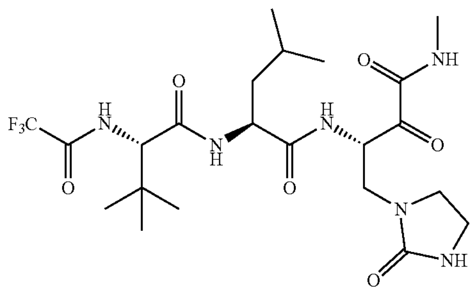 [SMILES: CNC(=O)C(=O)[C@H](CN1CCNC1=O)NC(=O)[C@H](CC(C)C)NC(=O)[C@@H](NC(=O)C(F)(F)F)C(C)(C)C] | (S)-2-((S)-3,3-dimethyl-2-(2,2,2-trifluoroacetamido)butanamido)-4-methyl-N-((S)-4-(methylamino)-3,4-dioxo-1-(2-oxoimidazolidin-1-yl)butan-2-yl)pentanamide |
| 11 | 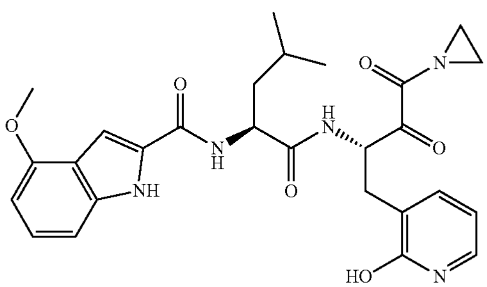 [SMILES: COc1cccc2[nH]c(C(=O)N[C@@H](CC(C)C)C(=O)N[C@@H](Cc3cccnc3O)C(=O)C(=O)N3CC3)cc12] | N-((S)-(((S)-4-(aziridin-1-yl)-1-(2-hydroxypyridin-3-yl)-3,4-dioxobutan-2-yl)amino)-4-methyl-1-oxopentan-2-yl)-4-methoxy-1H-indole-2-carboxamide |
| 12 | 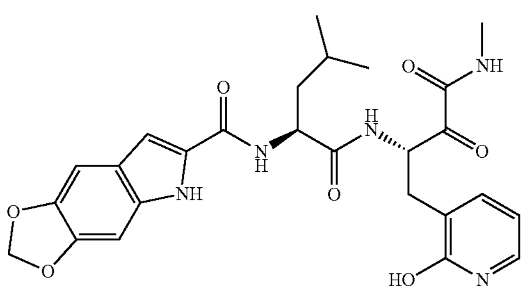 [SMILES: CNC(=O)C(=O)[C@H](Cc1cccnc1O)NC(=O)[C@H](CC(C)C)NC(=O)c1cc2cc3c(cc2[nH]1)OCO3] | N-((S)-1-(((S)-1-(2-hydroxypyridin-3-yl)-4-(methylamino)-3,4-dioxobutan-2-yl)amino)-4-methyl-1-oxopentan-2-yl)-5H-[1,3]dioxolo[4,5-f]indole-6-carboxamide |
| 13 | 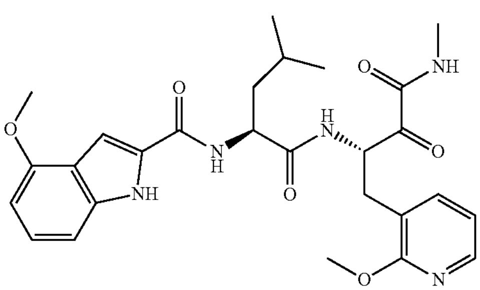 [SMILES: CNC(=O)C(=O)[C@H](Cc1cccnc1OC)NC(=O)[C@H](CC(C)C)NC(=O)c1cc2c(OC)cccc2[nH]1] | 4-methoxy-N-((S)-1-(((S)-1-(2-methoxypyridin-3-yl)-4-(methylamino)-3,4-dioxobutan-2-yl)amino)-4-methyl-1-oxopentan-2-yl)-1H-indole-2-carboxamide |

TABLE 1-continued

| Cmpd. No. | Structure | Name |
|---|---|---|
| 14 | 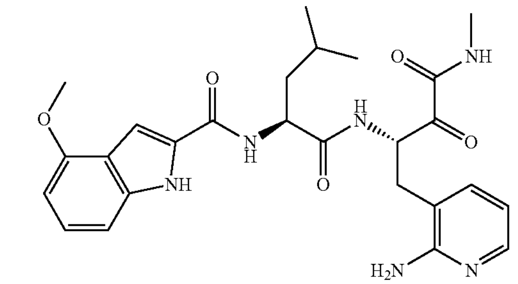 [SMILES: CNC(=O)C(=O)[C@H](Cc1cccnc1N)NC(=O)[C@H](CC(C)C)NC(=O)c1cc2c(OC)cccc2[nH]1] | N-((S)-1-(((S)-1-(2-aminopyridin-3-yl)-4-(methylamino)-3,4-dioxobutan-2-yl)amino)-4-methyl-1-oxopentan-2-yl)-4-methoxy-1H-indole-2-carboxamide |
| 15 | 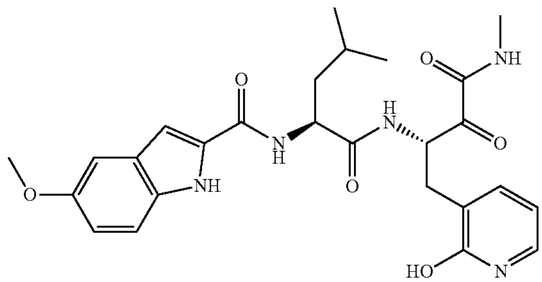 [SMILES: CNC(=O)C(=O)[C@H](Cc1cccnc1O)NC(=O)[C@H](CC(C)C)NC(=O)c1cc2cc(OC)ccc2[nH]1] | N-((S)-1-(((S)-1-(2-hydroxypyridin-3-yl)-4-(methylamino)-3,4-dioxobutan-2-yl)amino)-4-methyl-1-oxopentan-2-yl)-5-methoxy-1H-indole-2-carboxamide |
| 16 | 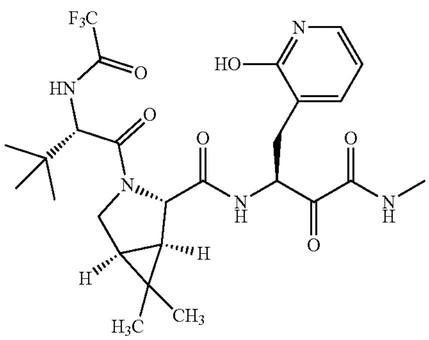 [SMILES: CNC(=O)C(=O)[C@H](Cc1cccnc1O)NC(=O)[C@@H]1[C@@H]2[C@H](CN1C(=O)[C@@H](NC(=O)C(F)(F)F)C(C)(C)C)C2(C)C] | (1R,2S,5S)-3-((S)-3,3-dimethyl-2-(2,2,2-trifluoroacetamido)butanoyl)-N-((S)-1-(2-hydroxypyridin-3-yl)-4-(methylamino)-3,4-dioxobutan-2-yl)-6,6-dimethyl-3-azabicyclo[3.1.0]hexane-2-carboxamide |
| 17 | 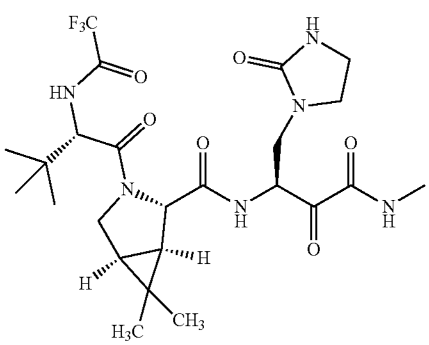 [SMILES: CNC(=O)C(=O)[C@H](CN1CCNC1=O)NC(=O)[C@@H]1[C@@H]2[C@H](CN1C(=O)[C@@H](NC(=O)C(F)(F)F)C(C)(C)C)C2(C)C] | (1R,2S,5S)-3-((S)-3,3-dimethyl-2-(2,2,2-trifluoroacetamido)butanoyl)-6,6-dimethyl-N-((S)-4-(methylamino)-3,4-dioxo-1-(2-oxoimidazolidin-1-yl)butan-2-yl)-3-azabicyclo[3.1.0]hexane-2-carboxamide |

Any combination of the groups described above for the various variables is contemplated herein. Throughout the specification, groups and substituents thereof can be chosen by one skilled in the field to provide stable moieties and compounds.

In some embodiments, a Compound of the Disclosure is present in the pharmaceutical composition as a pharmaceutically acceptable salt. In some embodiments, any compound described above is suitable for any method or composition described herein.

III. Forms of Compounds of the Disclosure

A. Isomers

In some aspects, Compounds of the Disclosure exist as geometric isomers. In some aspects, Compounds of the Disclosure possess one or more double bonds. Compounds of the Disclosure include all cis, trans, syn, anti, entgegen (E), and zusammen (Z) isomers as well as the corresponding mixtures thereof. In some situations, Compounds of the Disclosure exist as tautomers. Compounds of the Disclosure include all possible tautomers within the formulas described herein. For example, the following tautomers of $R^1$-1 of Formula I are encompassed by the present disclosure, e.g., when R[7] is, respectively, —OH or —NH$_2$:

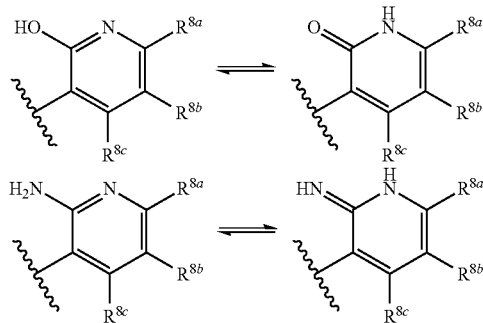

The equilibrium arrows are not intended to show the position of the equilibrium, only that an equilibrium exists between the two tautomeric forms of R[1]-1.

Compounds of the Disclosure possess one or more chiral centers and each center exists in the R configuration or S configuration. The Compounds of the Disclosure include all diastereomeric, enantiomeric, and epimeric forms as well as the corresponding mixtures thereof. In additional aspects of the compounds and methods provided herein, mixtures of enantiomers and/or diastereoisomers, resulting from a single preparative step, combination, or interconversion, are useful for the applications described herein. In some aspects, Compounds of the Disclosure are prepared as optically pure enantiomers by chiral chromatographic resolution of the racemic mixture. In some aspects, the Compounds of the Disclosure are prepared as their individual stereoisomers by reacting a racemic mixture of the compound with an optically active resolving agent to form a pair of diastereoisomeric compounds, separating the diastereomers, and recovering the optically pure enantiomers. In some aspects, dissociable complexes are preferred (e.g., crystalline diastereomeric salts). In some aspects, the diastereomers have distinct physical properties (e.g., melting points, boiling points, solubilities, reactivity, etc.) and are separated by taking advantage of these dissimilarities. In some aspects, the diastereomers are separated by chiral chromatography, or by separation/resolution techniques based upon differences in solubility. In some aspects, the optically pure enantiomer is then recovered, along with the resolving agent, by any practical means that does not result in racemization.

B. Labeled Compounds

In some aspects, Compounds of the Disclosure in their isotopically-labeled forms. In some aspects, the methods disclosed herein include methods of treating diseases by administering such isotopically-labeled compounds. In some aspects, the methods disclosed herein include methods of treating diseases by administering such isotopically-labeled compounds as pharmaceutical compositions. Thus, in some aspects, Compounds of the Disclosure include isotopically-labeled compounds, which are identical to those recited herein, but for the fact that one or more atoms are replaced by an atom having an atomic mass or mass number different from the atomic mass or mass number usually found in nature. Examples of isotopes that are incorporated into Compounds of the Disclosure include isotopes of hydrogen, carbon, nitrogen, oxygen, phosphorous, sulfur, fluorine, and chloride, such as $^2$H, $^3$H, $^{13}$C, $^{14}$C, $^{15}$N, $^{17}$O, $^{18}$O, $^{31}$P, $^{32}$P, $^{35}$S is F, and $^{36}$Cl, respectively. Compounds of the Disclosure that contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i.e., $^3$H and carbon-14, i.e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some aspects, the isotopically labeled Compounds of the Disclosure are prepared by any suitable method.

In some aspects, Compounds of the Disclosure are labeled by other means, including, but not limited to, the use of chromophores or fluorescent moieties, bioluminescent labels, or chemiluminescent labels.

C. Pharmaceutically Acceptable Salts

In some aspects, Compounds of the Disclosure exist as their pharmaceutically acceptable salts. In some aspects, the methods disclosed herein include methods of treating diseases by administering such pharmaceutically acceptable salts. In some aspects, the methods disclosed herein include methods of treating diseases by administering such pharmaceutically acceptable salts as pharmaceutical compositions.

In some aspects, Compounds of the Disclosure possess acidic or basic groups and therefore react with any of a number of inorganic or organic bases, and inorganic and organic acids, to form a pharmaceutically acceptable salt. In some aspects, these salts are prepared in situ during the final isolation and purification of the Compounds of the Disclosure, or by separately reacting a purified compound in its free form with a suitable acid or base, and isolating the salt thus formed.

D. Solvates

In some aspects, Compounds of the Disclosure exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the Compounds of the Disclosure are conveniently prepared or formed during the processes described herein. By way of example only, hydrates of the Compounds of the Disclosure are conveniently prepared by recrystallization from an aqueous/organic solvent mixture, using organic solvents including, but not limited to, dioxane, tetrahydrofuran, or MeOH. In addition, the compounds provided herein exist in unsolvated as well as solvated forms. In general, the solvated forms are considered equivalent to the unsolvated forms for the purposes of the compounds and methods provided herein.

IV. Synthesis of Compounds

In some embodiments, the synthesis of Compounds of the Disclosure are accomplished using means described in the chemical literature, using the methods described herein, or by a combination thereof. In addition, solvents, temperatures and other reaction conditions presented herein may vary.

In other embodiments, the starting materials and reagents used for the synthesis of Compounds of the Disclosure are synthesized or are obtained from commercial sources, such as, but not limited to, Sigma-Aldrich, Fischer Scientific (Fischer Chemicals), and Acros Organics.

herein may be derived from reactions and the reactions may be modified by the use of appropriate reagents and conditions, for the introduction of the various moieties found in the formulae as provided herein. As a guide the following synthetic methods may be utilized:

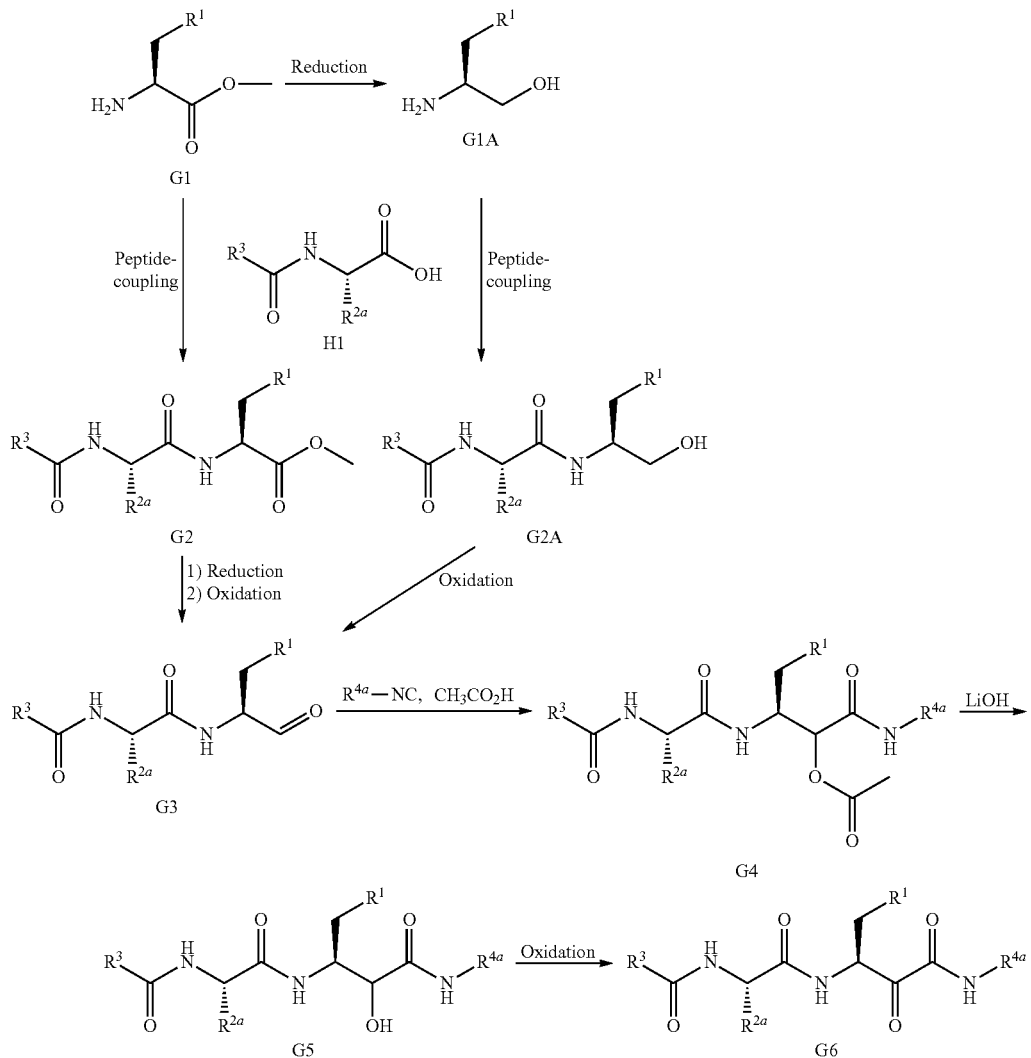

In further aspects, Compounds of the Disclosure, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis $3^{rd}$ Ed., (Wiley 1999) (all of which are incorporated by reference for such disclosure). General methods for the preparation of compound as disclosed Amino acid analog G1 is coupled with peptide H1 in the presence of an activator such as EDC-Cl (1-ethyl-3-(3-dimethylaminopropyl)carbodiimide), an additive to suppress isomerization such as HOBt (hydroxybenzotriazole), a base such as triethylamine, and a suitable organic solvent such as dimethylformamide.

The resulting dipeptide G2 is then reduced to a primary alcohol using a reductant (e.g. lithium aluminum hydride) and oxidized to aldehyde G3 in the presence of an oxidant such as a hypervalent iodine compound (e.g. Dess-Martin periodinane), a sulfonium (e.g. Swern oxidation), or hexavalent chromium (e.g. Collins reagent, PDC, or PCC). Alternatively, G1 is first reduced to alcohol G1A and coupled to peptide H1 using the above described conditions, and then oxidized to aldehyde G3. Formation of acetate G4 proceeds through exposure of aldehyde G3 to $R^{4a}$-substituted isocyanide in the presence of acetic acid. Exposure of acetate G4 to aqueous hydroxide (e.g. LiOH/$H_2O$) and oxidation of resulting hydroxyamide G5 with a suitable oxidant (e.g. PCC, Dess-Martin periodinane, Swern oxidation, TEMPO oxidation) provides the target α-ketoamide G6.

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a Pd$^0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

A detailed description of techniques applicable to the creation of protecting groups and their removal are described in Greene and Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure).

V. Methods of Treatment

In one aspect, provided herein is a method of treating or preventing a viral infection in an individual in need thereof comprising administering to the individual a therapeutically effective amount of a Compound of the Disclosure, or a pharmaceutical composition thereof, and, optionally, a therapeutically effective amount of a viral polymerase inhibitor, a protease inhibitor, a fusion inhibitor, a serine protease inhibitor, or a CYP3A4 inhibitor, or a combination thereof. In one aspect, the viral infection is caused by a virus in the Caliciviridae family, Picornaviridae family, or Coronaviridae family. In another aspect, the viral infection is caused by a virus in the Caliciviridae family. In another aspect, the virus in the Caliciviridae family is a Norwalk virus (NV), MD145 virus, or feline calicivirus (FCV). In another aspect, the viral infection is caused by a virus in the Picornaviridae family. In another aspect, the virus in the Picornaviridae family is human hepatitis A virus (HAV), poliomyelitis virus (PV), foot-and-mouth disease virus (FMDV), enterovirus 71 (EV71), human rhinovirus (HRV), or porcine teschovirus (PTV). In another aspect, the viral infection is caused by a virus in the Coronaviridae family. In another aspect, the virus in the Coronaviridae family is human coronavirus 229E, transmissible gastroenteritis virus (TGEV), murine hepatitis virus (MHV), bovine coronavirus (BCV), feline infectious peritonitis virus (FIPV), or severe acute respiratory syndrome coronavirus (SARS-CoV). In another aspect, the virus in the Coronaviridae family is severe acute respiratory syndrome coronavirus 2 (SARS-CoV-2). In another aspect, the viral polymerase inhibitor is Favipiravir, Bemnifosbuvir, AT-511, AT-527, Galidesivir, Remdesivir, Lufotrelvir, Molnupiravir, Sofosbuvir, or Ribavirin. In another aspect, the protease inhibitor is Lopinavir, Darunavir, or Atazanavir. In another aspect, the fusion inhibitor is Baricitinib or Umifenovir. In another aspect, the serine protease inhibitor is camostat mesylate. In another aspect, the CYP3A4 inhibitor is Ritonavir, Itraconazole or *Morinda citrifolia*.

In another aspect, provided herein is method of treating COVID-19 in an individual in need thereof comprising administering to the individual a therapeutically effective amount of a Compound of the Disclosure, or a pharmaceutical composition of thereof, and, optionally, a therapeutically effective amount of a viral polymerase inhibitor, a protease inhibitor, a fusion inhibitor, a serine protease inhibitor, or a CYP3A4 inhibitor, or a combination thereof. In another aspect, the viral polymerase inhibitor is Favipiravir, Bemnifosbuvir, AT-511, AT-527, Galidesivir, Remdesivir, Lufotrelvir, Molnupiravir, Sofosbuvir, or Ribavirin. In another aspect, the protease inhibitor is Lopinavir, Darunavir, or Atazanavir. In another aspect, the fusion inhibitor is Baricitinib or Umifenovir. In another aspect, the serine protease inhibitor is camostat mesylate. In another aspect, the CYP3A4 inhibitor is Ritonavir, Itraconazole or *Morinda citrifolia*.

In another aspect, provided herein is a Compound of the Disclosure, or a pharmaceutical composition thereof for use in treating or preventing a viral infection in an individual in need thereof, wherein the viral infection is caused by a virus in the Caliciviridae family, Picornaviridae family, or Coronaviridae family, and, optionally, wherein the Compound of the Disclosure, or the pharmaceutically acceptable composition thereof is to be administered in combination with a therapeutically effective amount of a viral polymerase inhibitor, a protease inhibitor, a fusion inhibitor, a serine protease inhibitor, or a CYP3A4 inhibitor, or a combination thereof. In another aspect, the viral infection is caused by a virus in the Caliciviridae family. In another aspect, the virus in the Caliciviridae family is a Norwalk virus (NV), MD145 virus, or feline calicivirus (FCV). In another aspect, the viral infection is caused by a virus in the Picornaviridae family. In another aspect, the virus in the Picornaviridae family is human hepatitis A virus (HAV), poliomyelitis virus (PV), foot-and-mouth disease virus (FMDV), enterovirus 71 (EV71), human rhinovirus (HRV), or porcine teschovirus (PTV). In another aspect, the viral infection is caused by a virus in the Coronaviridae family. In another aspect, the virus in the Coronaviridae family is human coronavirus 229E, transmissible gastroenteritis virus (TGEV), murine hepatitis virus (MHV), bovine coronavirus (BCV), feline infectious peritonitis virus (FIPV), or severe acute respiratory syndrome coronavirus (SARS-CoV). In another aspect, the coronavirus infection is severe acute respiratory syndrome coronavirus 2 (SARS-CoV-2). In another aspect, the viral polymerase inhibitor is Favipiravir, Bemnifosbuvir, AT-511, AT-527, Galidesivir, Remdesivir, Lufotrelvir, Molnupiravir, Sofosbuvir, or Ribavirin. In another aspect, the protease inhibitor is Lopinavir, Darunavir, or Atazanavir. In another aspect, the fusion inhibitor is Baricitinib or Umifenovir. In another aspect, the serine protease inhibitor is camostat mesylate. In another aspect, the CYP3A4 inhibitor is Ritonavir, Itraconazole or *Morinda citrifolia*.

In another aspect, provided herein is a Compound of the Disclosure, or a pharmaceutical composition thereof for use in treating COVID-19 in an individual in need thereof, and, optionally, wherein the Compound of the Disclosure, or the pharmaceutically acceptable composition thereof is to be administered in combination with a therapeutically effective amount of a viral polymerase inhibitor, a protease inhibitor, a fusion inhibitor, a serine protease inhibitor, or a CYP3A4 inhibitor, or a combination thereof. In another aspect, the viral polymerase inhibitor is Favipiravir, Bemnifosbuvir, AT-511, AT-527, Galidesivir, Remdesivir, Lufotrelvir, Molnupiravir, Sofosbuvir, or Ribavirin. In another aspect, the protease inhibitor is Lopinavir, Darunavir, or Atazanavir. In another aspect, the fusion inhibitor is Baricitinib or Umifenovir. In another aspect, the serine protease inhibitor is camostat mesylate. In another aspect, the CYP3A4 inhibitor is Ritonavir, Itraconazole or *Morinda citrifolia*.

In another aspect, provided herein is the use of a Compound of the Disclosure, or a pharmaceutical composition thereof in the manufacture of a medicament for treating or preventing a viral infection in an individual in need thereof, preventing a viral infection in an individual in need thereof, wherein the viral infection is caused by a virus in the Caliciviridae family, Picornaviridae family, or Coronaviridae family, and, optionally, wherein the Compound of the Disclosure, or the pharmaceutically acceptable composition thereof is to be administered in combination with a therapeutically effective amount of a viral polymerase inhibitor, a protease inhibitor, a fusion inhibitor, a serine protease inhibitor, or a CYP3A4 inhibitor, or a combination thereof. In another aspect, the viral infection is caused by a virus in the Caliciviridae family. In another aspect, the virus in the Caliciviridae family is a Norwalk virus (NV), MD145 virus, or feline calicivirus (FCV). In another aspect, the viral infection is caused by a virus in the Picornaviridae family. In another aspect, the virus in the Picornaviridae family is human hepatitis A virus (HAV), poliomyelitis virus (PV), foot-and-mouth disease virus (FMDV), enterovirus 71 (EV71), human rhinovirus (HRV), or porcine teschovirus (PTV). In another aspect, the viral infection is caused by a virus in the Coronaviridae family. In another aspect, the virus in the Coronaviridae family is human coronavirus 229E, transmissible gastroenteritis virus (TGEV), murine hepatitis virus (MHV), bovine coronavirus (BCV), feline infectious peritonitis virus (FIPV), or severe acute respiratory syndrome coronavirus (SARS-CoV). In another aspect, the coronavirus infection is severe acute respiratory syndrome coronavirus 2 (SARS-CoV-2). In another aspect, the viral polymerase inhibitor is Favipiravir, Bemnifosbuvir, AT-511, AT-527, Galidesivir, Remdesivir, Lufotrelvir, Molnupiravir, Sofosbuvir, or Ribavirin. In another aspect, the protease inhibitor is Lopinavir, Darunavir, or Atazanavir. In another aspect, the fusion inhibitor is Baricitinib or Umifenovir. In another aspect, the serine protease inhibitor is camostat mesylate. In another aspect, the CYP3A4 inhibitor is Ritonavir, Itraconazole or *Morinda citrifolia*.

In another aspect, provided herein is the use of a Compound of the Disclosure, or a pharmaceutical composition thereof in the manufacture of a medicament for treating COVID-19 in an individual in need thereof, and, optionally, wherein the Compound of the Disclosure, or the pharmaceutically acceptable composition thereof is to be administered in combination with a therapeutically effective amount of a viral polymerase inhibitor, a protease inhibitor, a fusion inhibitor, a serine protease inhibitor, or a CYP3A4 inhibitor, or a combination thereof. In another aspect, the viral polymerase inhibitor is Favipiravir, Bemnifosbuvir, AT-511, AT-527, Galidesivir, Remdesivir, Lufotrelvir, Molnupiravir, Sofosbuvir, or Ribavirin. In another aspect, the protease inhibitor is Lopinavir, Darunavir, or Atazanavir. In another aspect, the fusion inhibitor is Baricitinib or Umifenovir. In another aspect, the serine protease inhibitor is camostat mesylate. In another aspect, the CYP3A4 inhibitor is Ritonavir, Itraconazole or *Morinda citrifolia*.

In another aspect, provided herein is a method of treating or preventing a viral infection in an individual in need thereof comprising administering to the individual a therapeutically effective amount of a compound of Formula I':

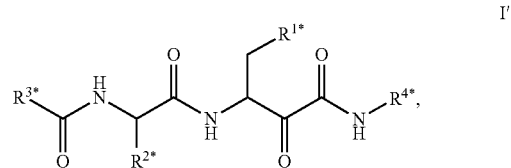

or a stereoisomer, tautomer, pharmaceutically acceptable salt or solvate thereof, wherein:

$R^{1*}$ is selected from

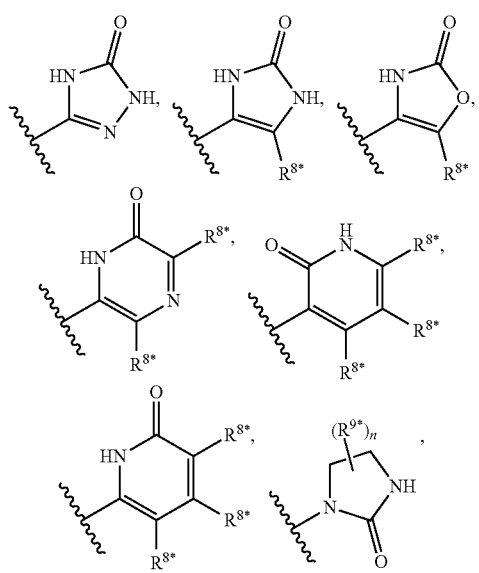

-continued

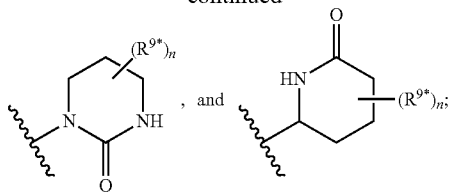
, and

R²* is selected from C₁₋₆ alkyl, C₂₋₆ alkenyl, C₂₋₆ alkynyl, C₃₋₆ cycloalkyl, —C₁₋₆ alkyl-C₃₋₆cycloalkyl, C₂₋₉ heterocycloalkyl, —C₁₋₆ alkyl-C₂₋₉ heterocycloalkyl, C₆₋₁₀ aryl, —C₁₋₆ alkyl-C₆₋₁₀ aryl, C₁₋₉ heteroaryl, and —C₁₋₆ alkyl-C₁₋₉ heteroaryl, wherein C₁₋₆ alkyl, C₂₋₆ alkenyl, C₂₋₆ alkynyl, C₃₋₆ cycloalkyl, —C₁₋₆ alkyl-C₃₋₆ cycloalkyl, C₂₋₉ heterocycloalkyl, —C₁₋₆ alkyl-C₂₋₉ heterocycloalkyl, C₆₋₁₀ aryl, —C₁₋₆ alkyl-C₆₋₁₀ aryl, C₁₋₉ heteroaryl, and —C₁₋₆ alkyl-C₁₋₉ heteroaryl are optionally substituted with one, two, three, or four groups selected from halogen, C₁₋₆ alkyl, C₁₋₆ haloalkyl, —OR⁵*, —N(R⁵*)(R⁶*), —C(O)R⁷*, —C(O)OR⁵*, —C(O)N(R⁵*)(R⁶*), —S(O)₂R⁷*, and —S(O)₂N(R⁵*)(R⁶*)—;

R³* is selected from C₃₋₆ cycloalkyl, C₂₋₉ heterocycloalkyl, C₆₋₁₀ aryl, and C₁₋₉ heteroaryl, wherein C₃₋₆ cycloalkyl, C₂₋₉ heterocycloalkyl, C₆₋₁₀ aryl, and C₁₋₉ heteroaryl are optionally substituted with one, two, three, or four groups selected from halogen, C₁₋₆ alkyl, C₁₋₆ haloalkyl, —OR⁵*, —N(R⁵*)(R⁶*), —C(O)R⁷*, —C(O)OR⁵*, —C(O)N(R⁵*)(R⁶*), —S(O)₂R⁷*, and —S(O)₂N(R⁵*)(R⁶*)—;

R⁴* is selected from C₁₋₆ alkyl, C₂₋₆ alkenyl, C₂₋₆ alkynyl, C₃₋₆ cycloalkyl, —C₁₋₆ alkyl-C₃₋₆cycloalkyl, C₂₋₉ heterocycloalkyl, —C₁₋₆ alkyl-C₂₋₉ heterocycloalkyl, C₆₋₁₀ aryl, —C₁₋₆ alkyl-C₆₋₁₀ aryl, C₁₋₉ heteroaryl, and —C₁₋₆ alkyl-C₁₋₉ heteroaryl, wherein C₁₋₆ alkyl, C₂₋₆ alkenyl, C₂₋₆ alkynyl, C₃₋₆ cycloalkyl, —C₁₋₆ alkyl-C₃₋₆ cycloalkyl, C₂₋₉ heterocycloalkyl, —C₁₋₆ alkyl-C₂₋₉ heterocycloalkyl, C₆₋₁₀ aryl, —C₁₋₆ alkyl-C₆₋₁₀ aryl, C₁₋₉ heteroaryl, and —C₁₋₆ alkyl-C₁₋₉ heteroaryl are optionally substituted with one, two, three, or four groups selected from halogen, C₁₋₆ alkyl, C₁₋₆ haloalkyl, —OR⁵*, —N(R⁵*)(R⁶*), —C(O)R⁷*, —C(O)OR⁵*, —C(O)N(R⁵*)(R⁶*), —S(O)₂R⁷*, and —S(O)₂N(R⁵*)(R⁶*)—;

each R⁵* is independently selected from hydrogen, C₁₋₆ alkyl, C₁₋₆ haloalkyl, C₂₋₆ alkenyl, C₂₋₆ alkynyl, C₃₋₆ cycloalkyl, C₂₋₉ heterocycloalkyl, C₆₋₁₀ aryl, and C₁₋₉ heteroaryl, wherein C₁₋₆ alkyl, C₂₋₆ alkenyl, C₂₋₆ alkynyl, C₃₋₆ cycloalkyl, C₂₋₉ heterocycloalkyl, C₆₋₁₀ aryl, and C₁₋₉ heteroaryl are optionally substituted with one, two, or three groups selected from halogen, C₁₋₆ alkyl, C₁₋₆ haloalkyl, C₁₋₆ alkoxy, C₃₋₆ cycloalkyl, C₂₋₉ heterocycloalkyl, C₆₋₁₀ aryl, and C₁₋₉ heteroaryl;

each R⁶* is independently selected from hydrogen, C₁₋₆ alkyl, and C₁₋₆ haloalkyl; and each R⁷* is independently selected C₁₋₆ alkyl, C₂₋₆ alkenyl, C₂₋₆ alkynyl, C₃₋₆ cycloalkyl, C₂₋₉ heterocycloalkyl, C₆₋₁₀ aryl, and C₁₋₉ heteroaryl, wherein C₁₋₆ alkyl, C₂₋₆ alkenyl, C₂₋₆ alkynyl, C₃₋₆ cycloalkyl, C₂₋₉ heterocycloalkyl, C₆₋₁₀ aryl, and C₁₋₉ heteroaryl are optionally substituted with one, two, or three groups selected from halogen, C₁₋₆ alkyl, C₁₋₆ haloalkyl, C₁₋₆ alkoxy, C₃₋₆ cycloalkyl, C₂₋₉ heterocycloalkyl, C₆₋₁₀ aryl, and C₁₋₉ heteroaryl;

each R⁸* is independently selected from hydrogen, halogen, C₁₋₆ alkyl, C₁₋₆ haloalkyl, —N(R⁵*)(R⁶*), —C(O)R⁷*, —C(O)OR⁵*, —C(O)N(R⁵*)(R⁶*), —S(O)₂R⁷*, and —S(O)₂N(R⁵*)(R⁶*)—; and each R⁹* is independently selected from halogen, C₁₋₆ alkyl, C₁₋₆ haloalkyl, —OR⁵*, —N(R⁵*)(R⁶*), —C(O)R⁷*, —C(O)OR⁵*, —C(O)N(R⁵*)(R⁶*), —S(O)₂R⁷*, and —S(O)₂N(R⁵*)(R⁶*) and n is 0, 1, 2, 3, or 4, wherein the viral infection is caused by a virus in the Caliciviridae family, Picornaviridae family, or Coronaviridae family.

In another aspect, the method comprises administering to the individual a therapeutically effective amount of a compound of Formula II':

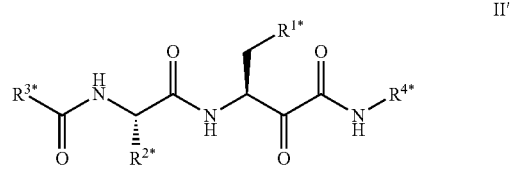

II' or a stereoisomer, tautomer, pharmaceutically acceptable salt or solvate thereof, wherein R¹*, R²*, R³*, and R⁴* are as defined in connection with Formula I'.

In another aspect, R¹* is selected from:

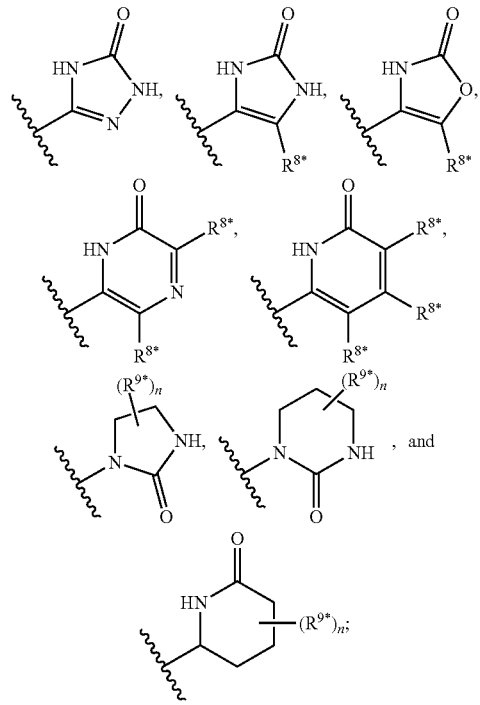

R²* is selected from C₁₋₆ alkyl, C₂₋₆ alkenyl, C₂₋₆ alkynyl, C₃₋₆ cycloalkyl, —C₁₋₆ alkyl-C₃₋₆cycloalkyl, C₂₋₉ heterocycloalkyl, —C₁₋₆ alkyl-C₂₋₉ heterocycloalkyl, C₆₋₁₀ aryl, —C₁₋₆ alkyl-C₆₋₁₀ aryl, C₁₋₉ heteroaryl, and —C₁₋₆ alkyl-C₁₋₉ heteroaryl, wherein C₁₋₆ alkyl, C₂₋₆ alkenyl, C₂₋₆ alkynyl, C₃₋₆ cycloalkyl, —C₁₋₆ alkyl-C₃₋₆ cycloalkyl, C₂₋₉ heterocycloalkyl, —C₁₋₆ alkyl-C₂₋₉ heterocycloalkyl, C₆₋₁₀ aryl, —C₁₋₆ alkyl-C₆₋₁₀ aryl, $C_{1-9}$ heteroaryl, and —$C_{1-6}$ alkyl-$C_{1-9}$ heteroaryl are optionally substituted with one, two, three, or four groups selected from halogen, $C_{1-6}$ alkyl, $C_{1-6}$ haloalkyl, —$OR^{5*}$, —$N(R^{5*})(R^{6*})$, —$C(O)R^{7*}$, —$C(O)OR^{5*}$, —$C(O)N(R^{5*})(R^{6*})$, —$S(O)_2R^{7*}$, and —$S(O)_2N(R^{5*})(R^{6*})$—;

$R^{3*}$ is selected from $C_{3-6}$ cycloalkyl, $C_{2-9}$ heterocycloalkyl, $C_{6-10}$ aryl, and $C_{1-9}$ heteroaryl, wherein $C_{3-6}$ cycloalkyl, $C_{2-9}$ heterocycloalkyl, $C_{6-10}$ aryl, and $C_{1-9}$ heteroaryl are optionally substituted with one, two, three, or four groups selected from halogen, $C_{1-6}$ alkyl, $C_{1-6}$ haloalkyl, —$OR^{5*}$, —$N(R^{5*})(R^{6*})$, —$C(O)R^{5*}$, —$C(O)OR^{5*}$, —$C(O)N(R^{5*})(R^{6*})$, —$S(O)_2R^{7*}$, and —$S(O)_2N(R^{5*})(R^{6*})$—;

$R^{4*}$ is selected from $C_{1-6}$ alkyl, $C_{2-6}$ alkenyl, $C_{2-6}$ alkynyl, $C_{3-6}$ cycloalkyl, —$C_{1-6}$ alkyl-$C_{3-6}$cycloalkyl, $C_{2-9}$ heterocycloalkyl, —$C_{1-6}$ alkyl-$C_{2-9}$ heterocycloalkyl, $C_{6-10}$ aryl, —$C_{1-6}$ alkyl-$C_{6-10}$ aryl, $C_{1-9}$ heteroaryl, and —$C_{1-6}$ alkyl-$C_{1-9}$ heteroaryl, wherein $C_{1-6}$ alkyl, $C_{2-6}$ alkenyl, $C_{2-6}$ alkynyl, $C_{3-6}$ cycloalkyl, —$C_{1-6}$ alkyl-$C_{3-6}$ cycloalkyl, $C_{2-9}$ heterocycloalkyl, —$C_{1-6}$ alkyl-$C_{2-9}$ heterocycloalkyl, $C_{6-10}$ aryl, —$C_{1-6}$ alkyl-$C_{6-10}$ aryl, $C_{1-9}$ heteroaryl, and —$C_{1-6}$ alkyl-$C_{1-9}$ heteroaryl are optionally substituted with one, two, three, or four groups selected from halogen, $C_{1-6}$ alkyl, $C_{1-6}$ haloalkyl, —$OR^{5*}$, —$N(R^{5*})(R^{6*})$, —$C(O)R^{7*}$, —$C(O)OR^{5*}$, —$C(O)N(R^{5*})(R^{6*})$, —$S(O)_2R^{7*}$, and —$S(O)_2N(R^{5*})(R^{6*})$—;

each $R^{5*}$ is independently selected from hydrogen, $C_{1-6}$ alkyl, $C_{1-6}$ haloalkyl, $C_{2-6}$ alkenyl, $C_{2-6}$ alkynyl, $C_{3-6}$ cycloalkyl, $C_{2-9}$ heterocycloalkyl, $C_{6-10}$ aryl, and $C_{1-9}$ heteroaryl, wherein $C_{1-6}$ alkyl, $C_{2-6}$ alkenyl, $C_{2-6}$ alkynyl, $C_{3-6}$ cycloalkyl, $C_{2-9}$ heterocycloalkyl, $C_{6-10}$ aryl, and $C_{1-9}$ heteroaryl are optionally substituted with one, two, or three groups selected from halogen, $C_{1-6}$ alkyl, $C_{1-6}$ haloalkyl, $C_{1-6}$ alkoxy, $C_{3-6}$ cycloalkyl, $C_{2-9}$ heterocycloalkyl, $C_{6-10}$ aryl, and $C_{1-9}$ heteroaryl;

each $R^{6*}$ is independently selected from hydrogen, $C_{1-6}$ alkyl, and $C_{1-6}$ haloalkyl; and each $R^{7*}$ is independently selected $C_{1-6}$ alkyl, $C_{2-6}$ alkenyl, $C_{2-6}$ alkynyl, $C_{3-6}$cycloalkyl, $C_{2-9}$ heterocycloalkyl, $C_{6-10}$ aryl, and $C_{1-9}$ heteroaryl, wherein $C_{1-6}$ alkyl, $C_{2-6}$ alkenyl, $C_{2-6}$ alkynyl, $C_{3-6}$ cycloalkyl, $C_{2-9}$ heterocycloalkyl, $C_{6-10}$ aryl, and $C_{1-9}$ heteroaryl are optionally substituted with one, two, or three groups selected from halogen, $C_{1-6}$ alkyl, $C_{1-6}$ haloalkyl, $C_{1-6}$ alkoxy, $C_{3-6}$ cycloalkyl, $C_{2-9}$ heterocycloalkyl, $C_{6-10}$ aryl, and $C_{1-9}$ heteroaryl;

each $R^{5*}$ is independently selected from hydrogen, halogen, $C_{1-6}$ alkyl, $C_{1-6}$ haloalkyl, —$OR^{5*}$, —$N(R^{5*})(R^{6*})$, —$C(O)R^{7*}$, —$C(O)OR^{5*}$, —$C(O)N(R^{5*})(R^{6*})$, —$S(O)_2R^{7*}$, and —$S(O)_2N(R^{5*})(R^{6*})$—; and each $R^{9*}$ is independently selected from halogen, $C_{1-6}$ alkyl, $C_{1-6}$ haloalkyl, —$OR^{5*}$, —$N(R^{5*})(R^{6*})$, —$C(O)R^{7*}$, —$C(O)OR^{5*}$, —$C(O)N(R^{5*})(R^{6*})$, —$S(O)_2R^{7*}$, and —$S(O)_2N(R^{5*})(R^{6*})$— and n is 0, 1, 2, 3, or 4.

In another aspect, $R^{4*}$ is selected from $C_{1-6}$ alkyl, $C_{3-6}$ cycloalkyl, —$C_{1-6}$ alkyl-$C_{3-6}$cycloalkyl, $C_{6-10}$ aryl, —$C_{1-6}$ alkyl-$C_{6-10}$ aryl, $C_{1-9}$ heteroaryl, and —$C_{1-6}$ alkyl-$C_{1-9}$ heteroaryl, wherein $C_{1-6}$ alkyl, $C_{3-6}$ cycloalkyl, —$C_{1-6}$ alkyl-$C_{3-6}$ cycloalkyl, $C_{6-10}$ aryl, —$C_{1-6}$ alkyl-$C_{6-10}$ aryl, $C_{1-9}$ heteroaryl, and —$C_{1-6}$ alkyl-$C_{1-9}$ heteroaryl are optionally substituted with one, two, three, or four groups selected from halogen, $C_{1-6}$ alkyl, $C_{1-6}$ haloalkyl, —$OR^{5*}$, —$N(R^{5*})(R^{6*})$, —$C(O)R^{7*}$, —$C(O)OR^{5*}$, —$C(O)N(R^{5*})(R^{6*})$, —$S(O)_2R^{7*}$, and —$S(O)_2N(R^{5*})(R^{6*})$—.

In another aspect, $R^{4*}$ is selected from $C_{3-6}$ cycloalkyl, —$C_{1-6}$ alkyl-$C_{3-6}$ cycloalkyl, $C_{6-10}$ aryl, and —$C_{1-6}$ alkyl-$C_{6-10}$ aryl, wherein $C_{3-6}$ cycloalkyl, —$C_{1-6}$ alkyl-$C_{3-6}$ cycloalkyl, $C_{6-10}$ aryl, and —$C_{1-6}$ alkyl-$C_{6-10}$ aryl are optionally substituted with one, two, three, or four groups selected from halogen, $C_{1-6}$ alkyl, $C_{1-6}$ haloalkyl, —$OR^{5*}$, —$N(R^{5*})(R^{6*})$, —$C(O)R^{7*}$, —$C(O)OR^{5*}$, —$C(O)N(R^{5*})(R^{6*})$, —$S(O)_2R^{7*}$, and —$S(O)_2N(R^{5*})(R^{6*})$—.

In another aspect, $R^{4*}$ is $C_{3-6}$ cycloalkyl optionally substituted with one, two, three, or four groups selected from halogen, $C_{1-6}$ alkyl, $C_{1-6}$ haloalkyl, —$OR^{5*}$, —$N(R^{5*})(R^{6*})$, —$C(O)R^{7*}$, —$C(O)OR^{5*}$, —$C(O)N(R^{5*})(R^{6*})$, —$S(O)_2R^{7*}$, and —$S(O)_2N(R^{5*})(R^{6*})$—.

In another aspect, $R^{4*}$ is unsubstituted $C_{3-6}$ cycloalkyl.

In another aspect, $R^{4*}$ is —$C_{1-6}$ alkyl-$C_{3-6}$ cycloalkyl optionally substituted with one, two, three, or four groups selected from halogen, $C_{1-6}$ alkyl, $C_{1-6}$ haloalkyl, —$OR^{5*}$, —$N(R^{5*})(R^{6*})$, —$C(O)R^{7*}$, —$C(O)OR^{5*}$, —$C(O)N(R^{5*})(R^{6*})$, —$S(O)_2R^{7*}$, and —$S(O)_2N(R^{5*})(R^{6*})$—.

In another aspect, $R^{4*}$ is unsubstituted —$C_{1-6}$ alkyl-$C_{3-6}$ cycloalkyl.

In another aspect, $R^{4*}$ is phenyl optionally substituted with one, two, three, or four groups selected from halogen, $C_{1-6}$ alkyl, $C_{1-6}$ haloalkyl, —$OR^{5*}$, —$N(R^{5*})(R^{6*})$, —$C(O)R^{7*}$, —$C(O)OR^{5*}$, —$C(O)N(R^{5*})(R^{6*})$, —$S(O)_2R^{7*}$, and —$S(O)_2N(R^{5*})(R^{6*})$—.

In another aspect, $R^{4*}$ is unsubstituted phenyl.

In another aspect, $R^{4*}$ is —$C_{1-6}$ alkyl-phenyl optionally substituted with one, two, three, or four groups selected from halogen, $C_{1-6}$ alkyl, $C_{1-6}$ haloalkyl, —$OR^{5*}$, —$N(R^{5*})(R^{6*})$, —$C(O)R^{7*}$, —$C(O)OR^{5*}$, —$C(O)N(R^{5*})(R^{6*})$, —$S(O)_2R^{7*}$, and —$S(O)_2N(R^{5*})(R^{6*})$—.

In another aspect, $R^{4*}$ is unsubstituted —$C_{1-6}$ alkyl-phenyl.

In another aspect, $R^{4*}$ is:

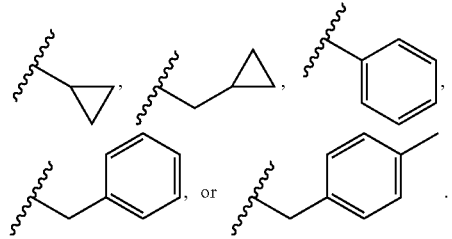

In another aspect, $R^{3*}$ is $C_{1-9}$ heteroaryl optionally substituted with one, two, three, or four groups selected from halogen, $C_{1-6}$ alkyl, $C_{1-6}$ haloalkyl, —$OR^{5*}$, —$N(R^{5*})(R^{6*})$, —$C(O)R^{7*}$, —$C(O)OR^{5*}$, —$C(O)N(R^{5*})(R^{6*})$, —$S(O)_2R^{7*}$, and —$S(O)_2N(R^{5*})(R^{6*})$—.

In another aspect, $R^{3*}$ is unsubstituted $C_{1-9}$ heteroaryl.

In another aspect, $R^{3*}$ is:

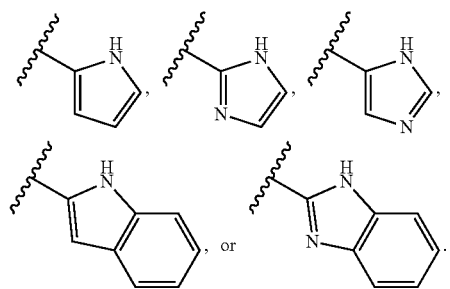

In another aspect, $R^{2*}$ is selected from $C_{1-6}$ alkyl, —$C_{1-6}$ alkyl-$C_{3-6}$ cycloalkyl, —$C_{1-6}$ alkyl-$C_{6-10}$ aryl, and —$C_{1-6}$ alkyl-$C_{1-9}$ heteroaryl, wherein $C_{1-6}$ alkyl, —$C_{1-6}$ alkyl-$C_{3-6}$ cycloalkyl, —$C_{1-6}$ alkyl-$C_{6-10}$ aryl, and —$C_{1-6}$ alkyl-$C_{1-9}$ heteroaryl are optionally substituted with one, two, three, or four groups selected from halogen, $C_{1-6}$ alkyl, $C_{1-6}$ haloalkyl, —$OR^{5*}$, —$N(R^{5*})(R^{6*})$, —$C(O)R^{7}$, —$C(O)OR^{5*}$, —$C(O)N(R^{5*})(R^{6*})$, —$S(O)_2R^{7*}$, and —$S(O)_2N(R^{5*})(R^{6*})$—.

In another aspect, $R^{2*}$ is $C_{1-6}$ alkyl optionally substituted with one, two, three, or four groups selected from halogen, $C_{1-6}$ alkyl, $C_{1-6}$ haloalkyl, —$OR^{5*}$, —$N(R^{5*})(R^{6*})$, —$C(O)R^{7*}$, —$C(O)OR^{5*}$, —$C(O)N(R^{5*})(R^{6*})$, —$S(O)_2R^{7*}$, and —$S(O)_2N(R^{5*})(R^{6*})$—.

In another aspect, $R^{2*}$ is unsubstituted $C_{1-6}$ alkyl.

In another aspect, $R^{2*}$ is —$C_{1-6}$ alkyl-$C_{3-6}$ cycloalkyl optionally substituted with one, two, three, or four groups selected from halogen, $C_{1-6}$ alkyl, $C_{1-6}$ haloalkyl, —$OR^{5*}$, —$N(R^{5*})(R^{6*})$, —$C(O)R^{7*}$, —$C(O)OR^{5*}$, —$C(O)N(R^{5*})(R^{6*})$, —$S(O)_2R^{7*}$, and —$S(O)_2N(R^{5*})(R^{6*})$—.

In another aspect, $R^{2*}$ is unsubstituted —$C_{1-6}$ alkyl-$C_{3-6}$ cycloalkyl.

In another aspect, $R^{2*}$ is —$C_{1-6}$ alkyl-phenyl optionally substituted with one, two, three, or four groups selected from halogen, $C_{1-6}$ alkyl, $C_{1-6}$ haloalkyl, —$OR^{5*}$, —$N(R^{5*})(R^{6*})$, —$C(O)R^{7*}$, —$C(O)OR^{5*}$, —$C(O)N(R^{5*})(R^{6*})$, —$S(O)_2R^{7*}$, and —$S(O)_2N(R^{5*})(R^{6*})$—.

In another aspect, $R^{2*}$ is unsubstituted —$C_{1-6}$ alkyl-phenyl.

In another aspect, $R^{2*}$ is —$C_{1-6}$ alkyl-$C_{1-9}$ heteroaryl optionally substituted with one, two, three, or four groups selected from halogen, $C_{1-6}$ alkyl, $C_{1-6}$ haloalkyl, —$OR^{5*}$, —$N(R^{5*})(R^{6*})$, —$C(O)R^{7*}$, —$C(O)OR^{5*}$, —$C(O)N(R^{5*})(R^{6*})$, —$S(O)_2R^{7*}$, and —$S(O)_2N(R^{5*})(R^{6*})$—.

In another aspect, $R^{2*}$ is unsubstituted —$C_{1-6}$ alkyl-$C_{1-9}$ heteroaryl.

In another aspect, $R^{2*}$ is —$CH_3$, —$CH_2CH_3$, —$C(H)(CH_3)_2$, —$CH_2C(H)(CH_3)_2$,

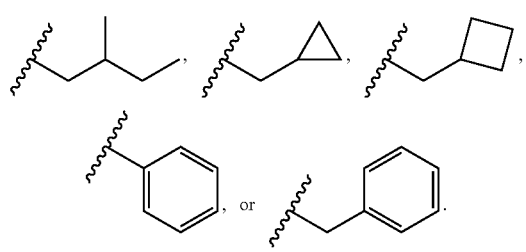

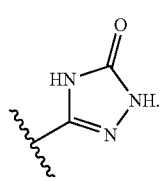 [SMILES: *c1n[nH]c(=O)[nH]1]

In another aspect, $R^{1*}$ is:

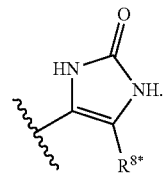

In another aspect, $R^{1*}$ is:

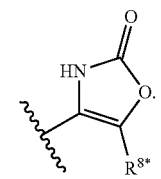

In another aspect, $R^{1*}$ is:

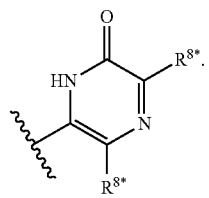

In another aspect, $R^{1*}$ is:

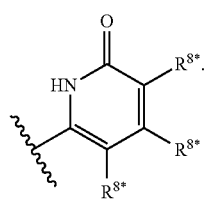

In another aspect, $R^{1*}$ is:

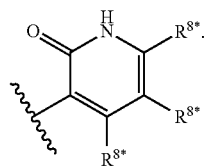

In another aspect, each $R^{5*}$ is hydrogen.

In another aspect, $R^{1*}$ is:

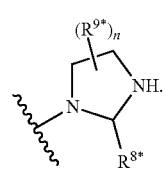

In another aspect, R¹* is:
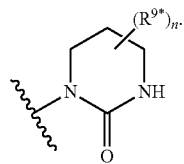
In another aspect, R¹* is:
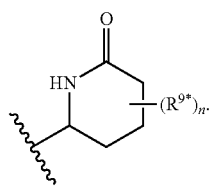
In another aspect, n is 0.
In another aspect, the compound is selected from:
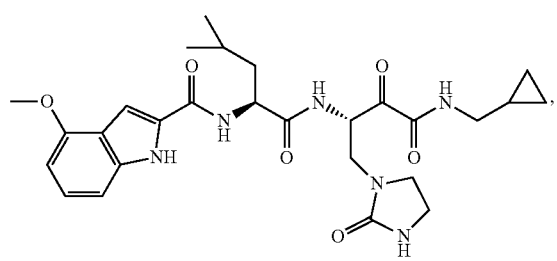
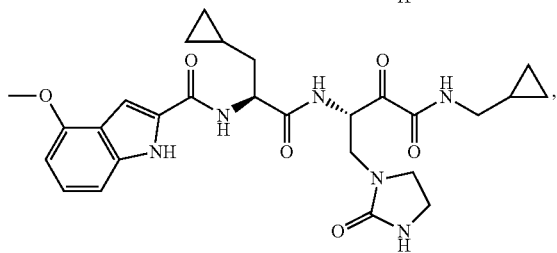
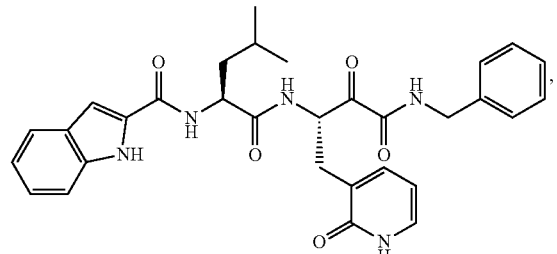
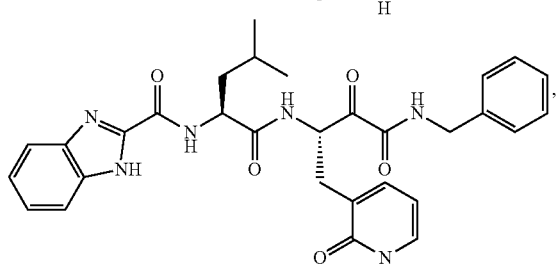
-continued
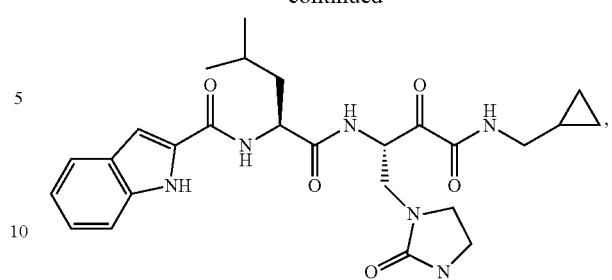
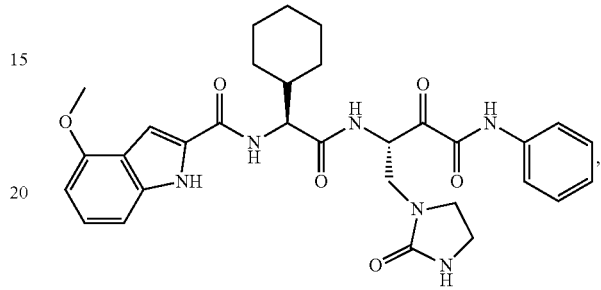
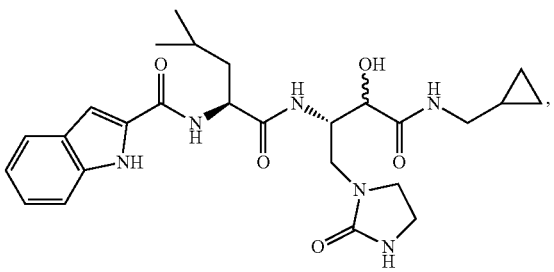
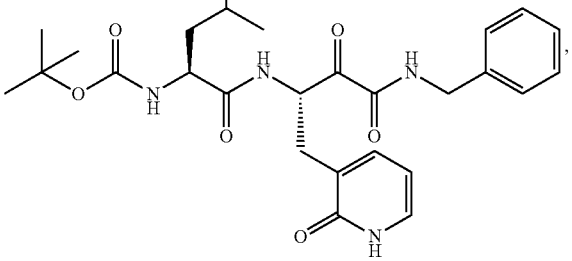
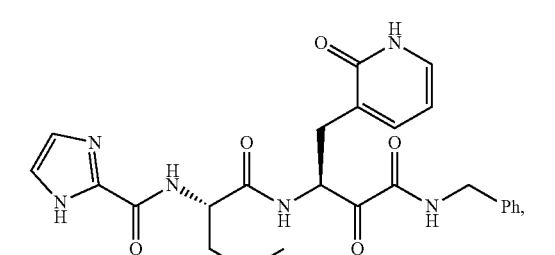
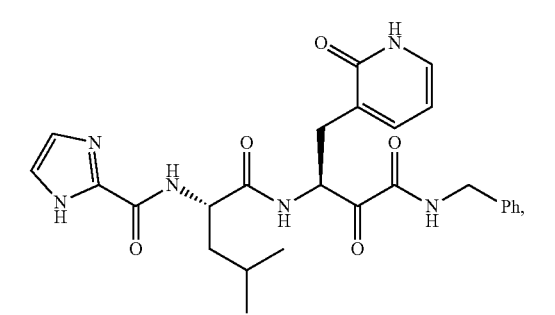

-continued
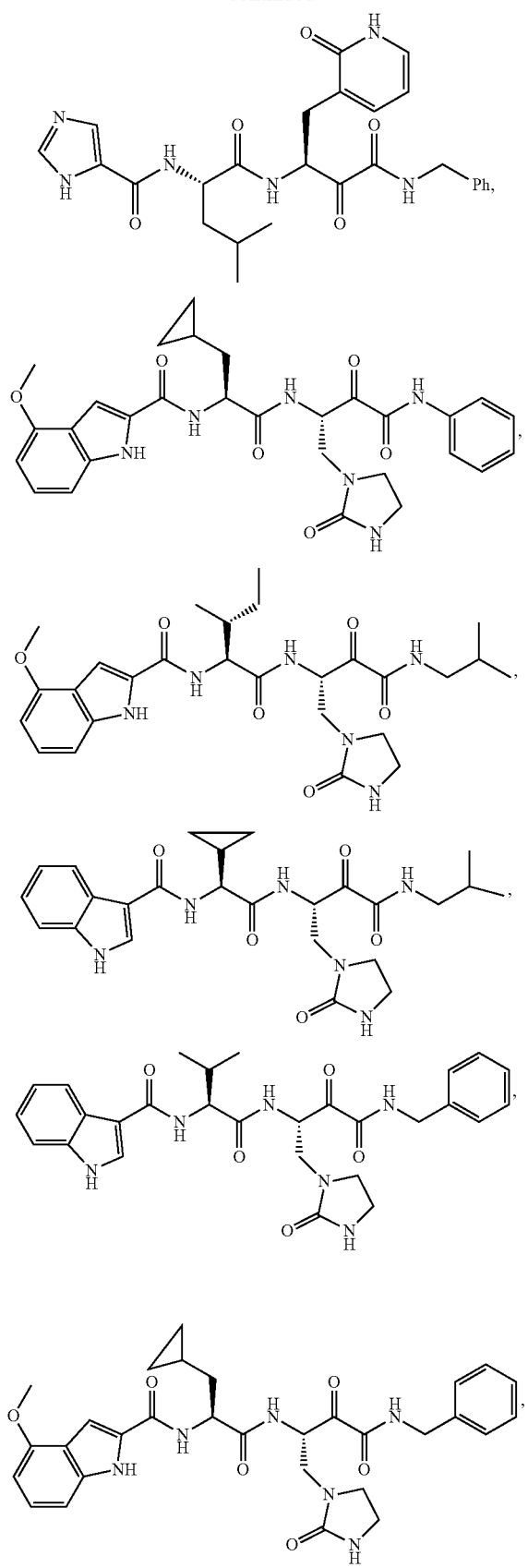
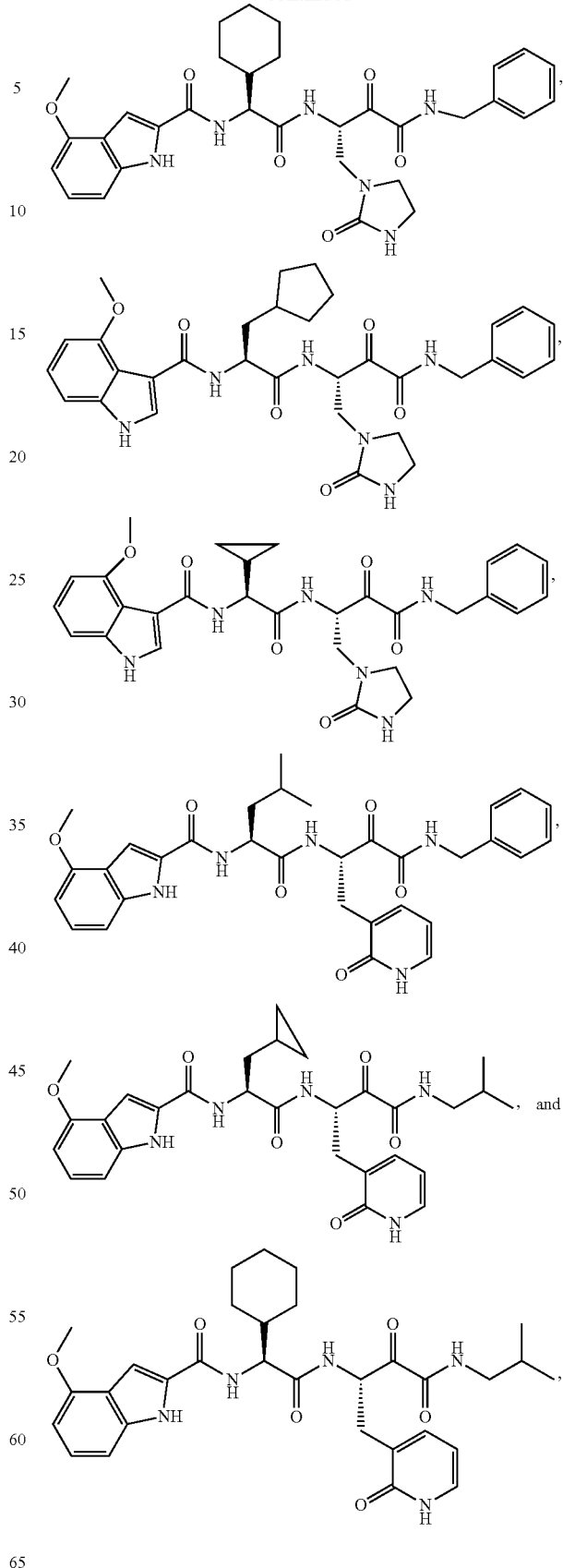
or a stereoisomer, tautomer, pharmaceutically acceptable salt or solvate thereof.

In another aspect, the viral infection is caused by a virus in the Caliciviridae family.

In another aspect, the virus in the Caliciviridae family is a Norwalk virus (NV), MD145 virus, or feline calicivirus (FCV).

In another aspect, the viral infection is caused by a virus in the Picornaviridae family.

In another aspect, the virus in the Picornaviridae family is human hepatitis A virus (HAV), poliomyelitis virus (PV), foot-and-mouth disease virus (FMDV), enterovirus 71 (EV71), human rhinovirus (HRV), or porcine teschovirus (PTV).

In another aspect, the viral infection is caused by a virus in the Coronaviridae family.

In another aspect, the virus in the Coronaviridae family is human coronavirus 229E, transmissible gastroenteritis virus (TGEV), murine hepatitis virus (MHV), bovine coronavirus (BCV), feline infectious peritonitis virus (FIPV), or severe acute respiratory syndrome coronavirus (SARS-CoV).

In another aspect, virus in the Coronaviridae family is severe acute respiratory syndrome coronavirus 2 (SARS-CoV-2).

In another aspect, the viral polymerase inhibitor is Favipiravir, Bemnifosbuvir, AT-511, AT-527, Galidesivir, Remdesivir, Lufotrelvir, Molnupiravir, Sofosbuvir, or Ribavirin.

In another aspect, the protease inhibitor is Lopinavir, Darunavir, or Atazanavir.

In another aspect, the fusion inhibitor is Baricitinib or Umifenovir.

In another aspect, the serine protease inhibitor is camostat mesylate.

In another aspect, the CYP3A4 inhibitor is Ritonavir, Itraconazole or *Morinda citrifolia*.

In another aspect, provided herein is a compound of Formula I' or II', or a pharmaceutical composition thereof for use in treating or preventing a viral infection in an individual in need thereof, wherein the compound of Formula I' or II', or the pharmaceutically acceptable composition thereof is to be administered in combination with a therapeutically effective amount of a viral polymerase inhibitor, a protease inhibitor, a fusion inhibitor, a serine protease inhibitor, or a CYP3A4 inhibitor, or a combination thereof, wherein the viral infection is caused by a virus in the Caliciviridae family, Picornaviridae family, or Coronaviridae family.

In another aspect, provided herein is the use of a compound of Formula I' or II', or a pharmaceutical composition thereof, in the manufacture of a medicament for treating or preventing a viral infection in an individual in need thereof, preventing a viral infection in an individual in need thereof, wherein the viral infection is caused by a virus in the Caliciviridae family, Picornaviridae family, or Coronaviridae family, and the compound of Formula I' or II', or the pharmaceutically acceptable composition thereof is to be administered in combination with a therapeutically effective amount of a viral polymerase inhibitor, a protease inhibitor, a fusion inhibitor, a serine protease inhibitor, or a CYP3A4 inhibitor, or a combination thereof.

VI. Pharmaceutical Compositions and Methods of Administration

The Compounds of the Disclosure and the compounds of Formula I' or II' described herein are administered to subjects in a biologically compatible form suitable for administration to treat or prevent diseases, disorders or conditions. Administration of the Compounds of the Disclosure or the compounds of Formula I' or II' as described herein can be in any pharmacological form including a therapeutically effective amount of a Compound of the Disclosure or a compound of Formula I' or II' alone or in combination with a pharmaceutically acceptable carrier.

In certain aspects, Compounds of the Disclosure or compounds of Formula I' or II' are administered as a pure chemical. In other embodiments, Compounds of the Disclosure or compounds of Formula I' or II' are combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, PA (2005)).

Accordingly, provided herein is a pharmaceutical composition comprising at least one Compound of the Disclosure or compound of Formula I' or II' together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

In some aspects, provided herein is a pharmaceutical composition comprising a pharmaceutically acceptable carrier and a Compound of the Disclosure. In some aspects, provided herein is a pharmaceutical composition consisting essentially of a pharmaceutically acceptable carrier and a Compound of the Disclosure.

In certain aspects, a Compound of the Disclosure or a compound of Formula I' or II' is substantially pure, in that it contains less than about 5%, or less than about 1%, or less than about 0.1%, of other organic small molecules, such as contaminating intermediates or by-products that are created, for example, in one or more of the steps of a synthesis method.

Compounds of the Disclosure or compounds of Formula I' or II', and formulations thereof can be administered by any suitable route to an individual. These formulations include those suitable for oral, topical, buccal, sublingual, parenteral (e.g., subcutaneous, intramuscular, intradermal, or intravenous), or aerosol administration. In one aspect, a Compound of the Disclosure or a compound of Formula I' or II' is administered by oral administration. In another aspect, a Compound of the Disclosure or a compound of Formula I' or II' is administered by buccal administration. In another aspect, a Compound of the Disclosure or a compound of Formula I' or II' is administered by sublingual administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some aspects, Compounds of the Disclosure are administered to subjects in a biologically compatible form suitable for topical administration to treat or prevent dermal diseases, disorders, or conditions. By "biologically compatible form suitable for topical administration" is meant a form of the Compound of the Disclosure or the compound of Formula I' or II' to be administered in which any toxic effects are outweighed by the therapeutic effects of the inhibitor. Administration of Compounds of the Disclosure or compounds of Formula I' or II' as described herein can be in any pharmacological form including a therapeutically effective amount of a Compound of the Disclosure or compound of Formula I' or II' alone or in combination with a pharmaceutically acceptable carrier.

Topical administration of Mpro cysteine protease inhibitors may be presented in the form of an aerosol, a semi-solid pharmaceutical composition, a powder, or a solution. By the term "a semi-solid composition" is meant an ointment, cream, salve, jelly, or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Chapter 67 of Remington's Pharmaceutical Sciences, 15th Edition (1975) published by Mack Publishing Company.

Dermal or skin patches are another method for transdermal delivery of the therapeutic or pharmaceutical compositions described herein. Patches can provide an absorption enhancer such as DMSO to increase the absorption of the compounds. Patches can include those that control the rate of drug delivery to the skin. Patches may provide a variety of dosing systems including a reservoir system or a monolithic system, respectively. The reservoir design may, for example, have four layers: the adhesive layer that directly contacts the skin, the control membrane, which controls the diffusion of drug molecules, the reservoir of drug molecules, and a water-resistant backing. Such a design delivers uniform amounts of the drug over a specified time period, the rate of delivery has to be less than the saturation limit of different types of skin. The monolithic design, for example, typically has only three layers: the adhesive layer, a polymer matrix containing the compound, and a water-proof backing. This design brings a saturating amount of drug to the skin. Thereby, delivery is controlled by the skin. As the drug amount decreases in the patch to below the saturating level, the delivery rate falls.

In one embodiment, the topical composition may, for example, take the form of hydrogel based on polyacrylic acid or polyacrylamide; as an ointment, for example with polyethyleneglycol (PEG) as the carrier, like the standard ointment DAB 8 (50% PEG 300, 50% PEG 1500); or as an emulsion, especially a microemulsion based on water-in-oil or oil-in-water, optionally with added liposomes. Suitable permeation accelerators (entraining agents) include sulphoxide derivatives such as dimethylsulphoxide (DMSO) or decylmethylsulphoxide (decyl-MSO) and transcutol (diethyleneglycolmonoethylether) or cyclodextrin; as well as pyrrolidones, for example 2-pyrrolidone, N-methyl-2-pyrrolidone, 2-pyrrolidone-5-carboxylic acid, or the biodegradable N-(2-hydroxyethyl)-2-pyrrolidone and the fatty acid esters thereof; urea derivatives such as dodecylurea, 1,3-didodecylurea, and 1,3-diphenylurea; and terpenes, for example D-limonene, menthone, a-terpinol, carvol, limonene oxide, or 1,8-cineol.

Ointments, pastes, creams and gels also can contain excipients, such as starch, tragacanth, cellulose derivatives, polyethylene glycols, silicones, bentonites, silicic acid, and talc, or mixtures thereof. Powders and sprays also can contain excipients such as lactose, talc, silicic acid, aluminum hydroxide, calcium silicates and polyamide powder, or mixtures of these substances. Solutions of nanocrystalline antimicrobial metals can be converted into aerosols or sprays by any of the known means routinely used for making aerosol pharmaceuticals. In general, such methods comprise pressurizing or providing a means for pressurizing a container of the solution, usually with an inert carrier gas, and passing the pressurized gas through a small orifice. Sprays can additionally contain customary propellants, such a chlorofluorohydrocarbons and volatile unsubstituted hydrocarbons, such as butane and propane.

The carrier can also contain other pharmaceutically-acceptable excipients for modifying or maintaining the pH, osmolarity, viscosity, clarity, color, sterility, stability, rate of dissolution, or odor of the formulation. The anti-skin aging compositions can also further comprise antioxidants, sun screens, natural retinoids (e.g., retinol), and other additives commonly found in skin treatment compositions.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

In some embodiments, powders and sprays contain, in addition to a subject composition, excipients such as lactose, talc, silicic acid, aluminum hydroxide, calcium silicates, and polyamide powder, or mixtures of these substances. In some embodiments, sprays additionally contain customary propellants, such as chlorofluorohydrocarbons and volatile unsubstituted hydrocarbons, such as butane and propane.

Compositions and compounds disclosed herein alternatively are administered by aerosol. This is accomplished by preparing an aqueous aerosol, liposomal preparation, or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient, or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants The dose of the composition comprising at least one compound described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). Optimal doses are generally determined using experimental models and/or clinical trials. In some embodiments, the optimal dose depends upon the body mass, weight, or blood volume of the patient.

Oral doses typically range from about 0.01 mg to about 1000 mg, one to four times, or more, per day. In one aspect, the unit dose may comprise from about 1 to about 1000 mg, e.g., about 0.01 to about 100 mg of a Compound of the Disclosure or a compound of Formula I' or II'. In another aspect, the unit oral is 0.05 mg, 1 mg, 3 mg, 5 mg, 7 mg, 9 mg, 10 mg, 12 mg, 14 mg, 15 mg, 17 mg, 20 mg, 22 mg, 25 mg, 27 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 200 mg, 250 mg, 300 mg, 350 mg, 400 mg, 450 mg, or 500 mg. The unit dose may be administered one or more times daily, e.g., as one or more tablets or capsules. The unit dose may be administered orally, intravenously, or subcutaneously to the subject. In practice, the physician determines the actual dosing regimen that is most suitable for an individual patient, which can vary with the age, weight, and response of the particular patient.

Dose administration can be repeated depending upon the pharmacokinetic parameters of the dosage formulation and the route of administration used.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the Mpro cysteine protease inhibitor and the particular therapeutic effect to be achieved and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the Mpro cysteine protease inhibitor activities disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such Mpro cysteine protease inhibitors can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Mpro cysteine protease inhibitors that exhibit large therapeutic indices are preferred. While Mpro cysteine protease inhibitors that exhibit toxic side effects may be used, care should be taken to design a delivery system that targets such inhibitors to the site of affected tissue in order to minimize potential damage to uninfected cells and, thereby, reduce side effects.

The data obtained from the cell culture assays and animal studies can be used in formulating a range of dosage for use in humans. The dosage of such Mpro cysteine protease inhibitors lies preferably within a range of circulating concentrations that include the $ED_{50}$ with little or no toxicity. The dosage may vary within this range depending upon the dosage form employed and the route of administration utilized. For any Mpro cysteine protease inhibitor used in a method described herein, the therapeutically effective dose can be estimated initially from cell culture assays. A dose may be formulated in animal models to achieve a circulating plasma concentration range that includes the $IC_{50}$ (i.e., the concentration of Mpro cysteine protease inhibitor that achieves a half-maximal inhibition of symptoms) as determined in cell culture. Such information can be used to more accurately determine useful doses in humans. Levels in plasma may be measured, for example, by high performance liquid chromatography.

EXAMPLES

The following examples are offered for purposes of illustration and are not intended to limit the scope of the claims provided herein. All literature citations in these examples and throughout this specification are incorporated herein by references for all legal purposes to be served thereby. The starting materials and reagents used for the synthesis of the Compounds of the Disclosure may be synthesized or can be obtained from commercial sources, such as, but not limited to, Sigma-Aldrich, Acros Organics, Fluka, and Fischer Scientific.

Standard abbreviations and acronyms as defined in *J. Org. Chem.* 2007 72(1): 23A-24A are used herein. Other abbreviations and acronyms used herein are as follows:

| AcOH | acetic acid |
| DCM | dichloromethane |
| DMF | dimethylformamide |
| DMP | Dess-Martin periodinane |
| EtOAc | ethyl acetate |
| EtOH | ethanol |
| eq | equivalent |
| HATU | (1-[bis(dimethylamino)methylene]-1H-1,2,3-triazolo[4,5-b]pyridinium 3-oxide hexafluorophosphate |
| HBTU | N,N,N',N'-tetramethyl-O-(1H-benzotriazol-1-yl)uronium hexafluorophosphate |
| HOAt | 1-Hydroxy-7-azabenzotriazole |
| LC-MS | liquid chromatography-mass spectrometry |
| MeOH | methanol |
| TEA | triethylamine |
| TFA | trifluoroacetic acid |
| THF | tetrahydrofuran |
| rt | room temperature |

Example 1

Synthesis of N—((S)-1-(((S)-1-(2-hydroxypyridin-3-yl)-4-(methylamino)-3,4-dioxobutan-2-yl)amino)-4-methyl-1-oxopentan-2-yl)-4-methoxy-1H-indole-2-carboxamide (Cpd. No. 1)

Step 1. Ester Formation

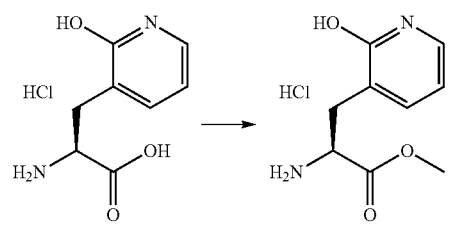

To 120 mL methanol was added 12 mL of acetyl chloride slowly at 0° C. The reaction mixture was stirred for 30 min. 2-hydroxypyridone-amino acid (6.8 mM; 1.5 g) of was added in one portion and stirred at 0° C. for 1 h and RT for 14 h. MS analysis indicated the absence of starting material and formation of product. The reaction mixture was concentrated and co-evaporated with toluene and several times with DCM to give methyl (S)-2-amino-3-(2-hydroxypyridin-3-yl)propanoate HCl as a white foamy solid.

Step 2. Synthesis of Boc-L-Leu-2-Pyridone Aminoacid Methyl Ester

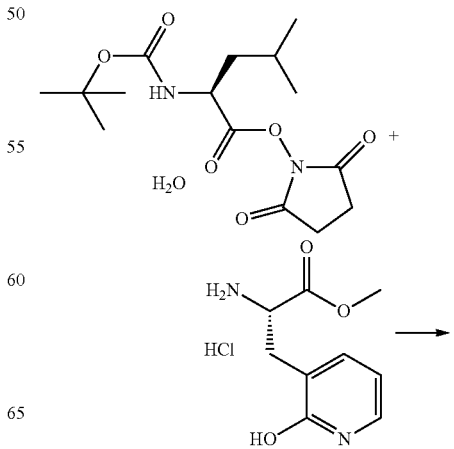

-continued

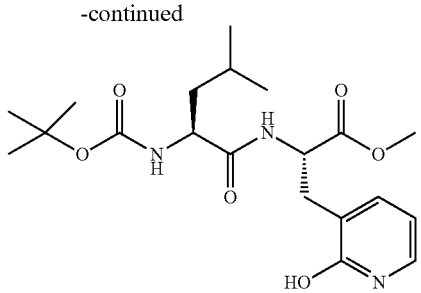

To a solution of 6.8 mM (all from previous reaction) of 2-hydroxypyridone amino acid methyl ester in 25 mL DMF was added 2.5 mL triethylamine followed by 7.5 mM (2.47 g) of solid Boc-L-Leu-OSu at RT. The reaction mixture was stirred for 36 h and then analyzed HPLC indicating the formation of only one new signal. The reaction mixture was concentrated and loaded to a column and eluted with 14% methanol. DCM to obtain three fractions. Fraction one contained the first spot as pure compound. Fraction three was the second spot but fraction two was a mixture of fraction one and two. MS analysis and HPLC indicated that it was a single compound with same mass. Fraction two was dissolved in DCM and washed with saturated ammonium chloride; the organic phase was dried over sodium sulfate and concentrated. TLC analysis indicated the presence of single compound. Fraction three was also washed with saturated ammonium chloride to obtain the product. In total 2 g (72%) of methyl (S)-2-((S)-2-((tert.-butoxycarbonyl) amino)-4-methylpentanamido)-3-(2-hydroxypyridin-3-yl) propanoate was obtained as a white solid.

Step 3. Ester Reduction

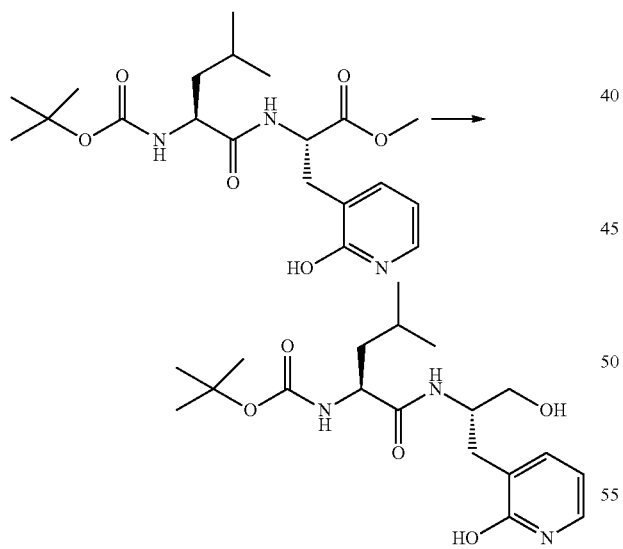

To a solution of 2.68 mM (1.1 g) methyl (S)-2-((S)-2-((tert.-butoxycarbonyl)amino)-4-methylpentanamido)-3-(2-hydroxypyridin-3-yl)propanoate in 20 mL THF and 2.4 mL ethanol were added slowly 2.2 mL of a 4 M solution of lithium borohydride in THF at RT. The reaction mixture was stirred for 30 min. TLC analysis (5% methanol. DCM) indicated the absence of starting material. The reaction mixture was quenched with a few drops of acetone, diluted with ethyl acetate and then washed with water to give 900 mg (88%) of tert-butyl ((S)-1-(((S)-1-hydroxy-3-(2-hydroxypyridin-3-yl)propan-2-yl)amino)-4-methyl-1-oxopentan-2-yl)carbamate as a white solid.

Step 4. Passerini Reaction

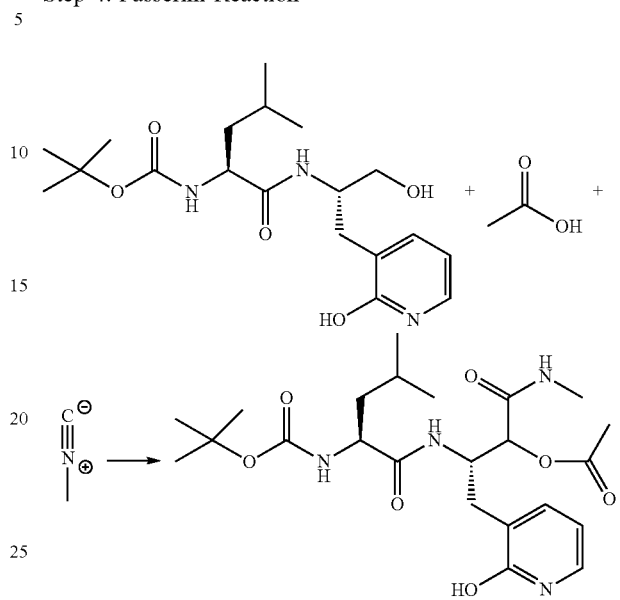

To a solution of 2.36 mM (900 mg) tert.-butyl ((S)-1-(((S)-1-hydroxy-3-(2-hydroxypyridin-3-yl)propan-2-yl) amino)-4-methyl-1-oxopentan-2-yl)carbamate in 20 mL DCM were added 150 μL methyl isonitrile and 140 μL acetic acid and 1.1 g Dess-Martin periodinane at RT. The reaction mixture was stirred for 24 h. TLC indicated the formation of new spot near the starting alcohol. The reaction mixture was filtered and concentrated. It was loaded to a column and eluted with 1-5% methanol. DCM to obtain 800 mg (70%) of (5S,8S)-5-((2-hydroxypyridin-3-yl)methyl)-8-isobutyl-12,12-dimethyl-3,7,10-trioxo-11-oxa-2,6,9-triazatridecan-4-yl acetate as a white solid. The product was confirmed by MS analysis. HPLC and TLC showed two spots of the diastereomers.

Step 5. Deprotection

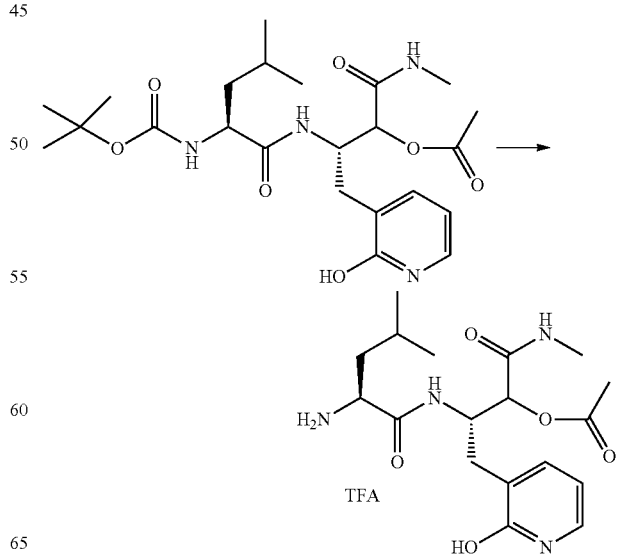

To a solution of 0.41 mM (200 mg) (5S,8S)-5-((2-hydroxypyridin-3-yl)methyl)-8-isobutyl-12,12-dimethyl-3,7,10-trioxo-11-oxa-212,6,9-triazatridecan-4-yl acetate in 6 mL DCM was added 2 mL TFA. The reaction mixture was stirred for 30 min. HPLC analysis indicated the completion of reaction. The reaction mixture was concentrated and co-evaporated with DCM several times and finally dried in high vacuum to give (3S)-3-((S)-2-amino-4-methylpentanamido)-4-(2-hydroxypyridin-3-yl)-1-(methylamino)-1-oxobutan-2-yl acetate as the TFA salt. The product was used in the next step without further purification.

Step 6. Coupling with Activated 4-Methoxyindol Carboxylic Acid

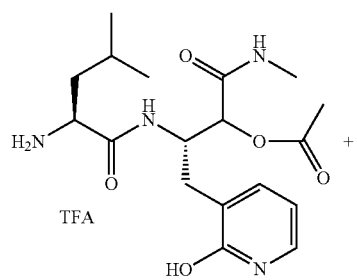

TFA

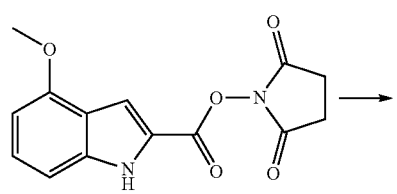

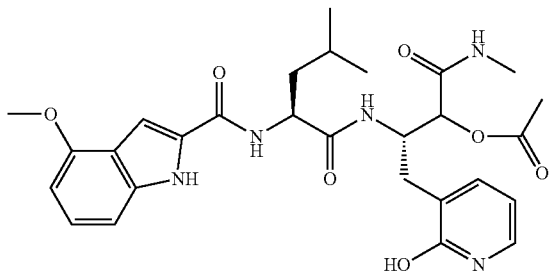

(3S)-3-((S)-2-amino-4-methylpentanamido)-4-(2-hydroxypyridin-3-yl)-1-(methylamino)-1-oxobutan-2-yl acetate TFA salt (0.41 mM; all from previous reaction) was dissolved in 5 mL DMF and 3.5 mM (0.4 mL) triethylamine was added. After stirring for 5 min at RT, 0.45 mM (130 mg) of the solid activated acid were added portion wise and the reaction mixture was stirred overnight. HPLC analysis indicated the formation of new peak near the starting material. The reaction mixture was concentrated and loaded to a small column. It was eluted with 0-6% methanol. DCM to give 130 mg (57%) of (3S)-4-(2-hydroxypyridin-3-yl)-3-((S)-2-(4-methoxy-1H-indole-2-carboxamido)-4-methylpentanamido)-1-(methylamino)-1-oxobutan-2-yl acetate as a white solid.

Step 7. Deprotection

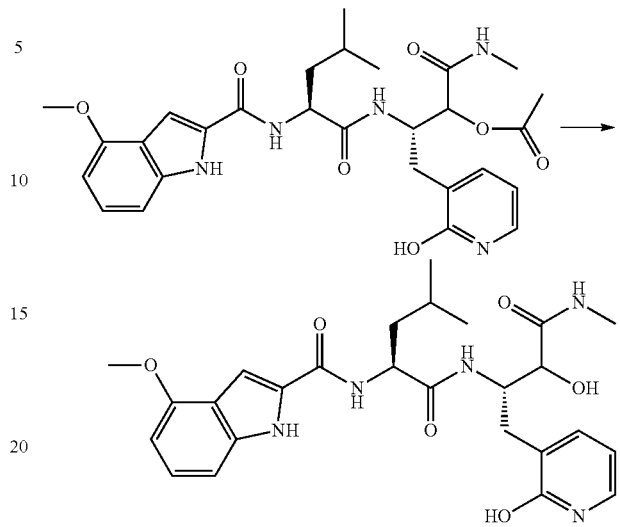

To a solution of 0.23 mM (130 mg) ((3S)-4-(2-hydroxypyridin-3-yl)-3-((S)-2-(4-methoxy-1H-indole-2-carboxamido)-4-methylpentanamido)-1-(methylamino)-1-oxobutan-2-yl acetate in 15 mL MeOH was added 0.3 mL of a saturated solution of $K_2CO_3$ at RT. The reaction mixture was stirred for 30 min. TLC (7% methanol:DCM) indicated the completion of the reaction. Saturated brine (30 mL) was added and extracted with 30 mL of DCM (3-times). The combined organic phases were dried over sodium sulfate and concentrated to obtain 110 mg (92%) of the crude alcohol (N-((2S)-1-(((2S)-3-hydroxy-1-(2-hydroxypyridin-3-yl)-4-(methylamino)-4-oxobutan-2-yl)amino)-4-methyl-1-oxopentan-2-yl)-4-methoxy-1H-indole-2-carboxamide). TLC showed a mixture of two diastereomers. MS confirmed the desired product.

Step 8. Oxidation with Dess-Martin Periodinane

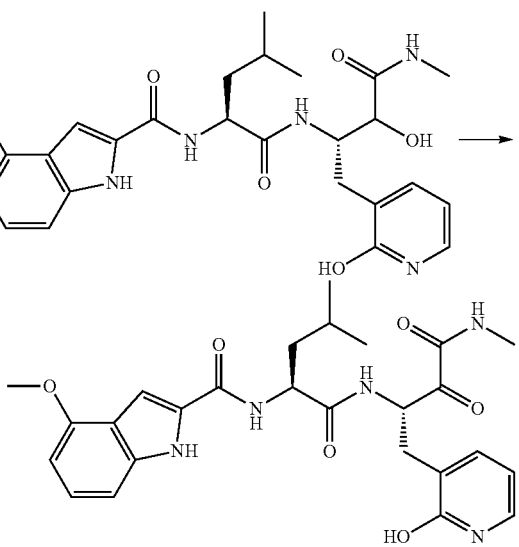

Cpd. No. 1

To a suspension of 0.21 mM (110 mg)N-((2S)-1-(((2S)-3-hydroxy-1-(2-hydroxypyridin-3-yl)-4-(methylamino)-4-oxobutan-2-yl)amino)-4-methyl-1-oxopentan-2-yl)-4-methoxy-1H-indole-2-carboxamide in 20 mL DCM was added 100 mg Dess-Martin periodinane at RT. The reaction mixture was stirred for 1 h. TLC (7% methanol:DCM) indicated the presence of little starting material along with formation of product. The suspension was filtered and concentrated. Column chromatography using 1-6% methanol:DCM gave 8 mg (8%) of N—((S)-1-(((S)-1-(2-hydroxypyridin-3-yl)-4-(methylamino)-3,4-dioxobutan-2-yl)amino)-4-methyl-1-oxopentan-2-yl)-4-methoxy-1H-indole-2-carboxamide as a slightly brown solid. MS confirmed the product.

Example 2

Mpro Enzyme Activity Assay

Representative Compounds of the Disclosure, PF-00835231, and PF-07321332 were tested for their capability to inhibit the SARS-CoV-2 main protease M$^{pro}$ by using a biochemical FRET-based M$^{pro}$ enzyme activity assay. Representative compounds of Formula I' and II' were also tested. See PCT/US2021/046311. Briefly, recombinant M$^{pro}$ protein (Ser1-Gln306; with proven proteolytic activity) was purchased from Biosynth Carbosynth (Staad, Switzerland). An EDANS- and Dabcyl-labeled peptide was purchased from Life Technologies GmbH (Darmstadt, Germany), and served as substrate peptide for M$^{pro}$ proteolytic cleavage allowing fluorescence resonance energy transfer (FRET) read-out. Due to the M$^{pro}$-mediated cleavage of the substrate peptide, the EDANS fluorescence ($\lambda$exc.=336 nm; $\lambda$em.=490 nm) becomes dequenched (from disappearing Dabcyl) and increases with increasing M$^{pro}$ activity. The assay buffer was 20 mM Tris buffer supplemented with 100 mM NaCl, and 1 mM EDTA, adjusted to pH 7.3 with 1N HCl. The test compounds were diluted from 20 mM stocks in DMSO; the stock of the substrate peptide was 250 μM in aqua bidest. The catalytic activity of the recombinant M$^{pro}$ enzyme was 20 U/mg. It was checked in advance that neither the assay buffer nor the M$^{pro}$ protein by itself emit fluorescence at 490 nm under 336 nm excitation. The basal emission of the uncleaved substrate peptide was subtracted from all results by baseline correction. The enzyme assay was carried out in black U-form half-area 96-wells. Each assay sample was finally composed of 0.4 μL substrate peptide stock (3× ad 20 μL assay buffer to yield finally 2 μM; 100 pmol), 0.1 μL Mpro enzyme (20 mU in assay buffer ad 20 μL) and 20 μL of 3× (in assay buffer) test compound dilution, resulting in a final sample volume of 60 μL. The final test compound concentrations were: 10 μM for compound fast-screening, and 0-200 μM for IC$_{50}$ determinations. Initially, Mpro enzyme and test compound was added and mixed in 96-well and pre-incubated for 30 min in the dark with 200 rpm swiveling at room temperature. Subsequently, the reaction was started by addition of the substrate peptide, and followed by a fluorescence kinetic ($\lambda$exc.=336 nm/$\lambda$em.=500 nm/CutOff=435 nm; 30 min with 2 min increment by using a SpectraMax M5 multiwell plate reader (Molecular Devices, San Jose, CA, USA). Pure assay buffer served as blank control, samples containing just Mpro enzyme and substrate peptide without test compound were measured as positive control, and samples containing heat-inactivated (10 min at 60° C.) Mpro enzyme and substrate peptide as negative control. Each data point was tested in technical duplicates and ≥3 biological replicates. Dose-response curves were analyzed by using GraphPad Prism 8.0 software resulting in IC$_{50}$ values. See Table 2.

TABLE 2

| Cpd. No. | Mpro inhibition IC$_{50}$ (μM) |
|---|---|
| 1 | 0.030 |
| 2 | 0.114 |
| PF-00835231 | 0.065 |
| PF-07321332 | 0.150 |

Example 3

In Vitro Cell Viability Assay for Screening of Antiviral Compounds

Virus Culture

SARS-CoV-2 virus is isolated from patients in authorized German hospitals, e.g. University hospital Frankfurt/Main. SARS-CoV-2 is propagated in human CACO-2 cells and stored as stocks at −80° C. Virus titers (TCIP50/mL) are determined in dense but still subconfluent CACO-2 in 96-well.

Cell Viability Assay (Screening)

Test compounds are screened for anti-SARS-CoV-2 activity by using virus-infected CACO-2 cells. In brief, test compounds are diluted to appropriate concentrations in MEM supplemented with 1% FBS (reduced FBS content)-10 μM (0.1% DMSO finally) for initial compound fast-screening and 0.02-50 μM (max. 0.5% DMSO finally) for IC50 analyses, respectively—and added to dense but still subconfluent CACO-2 cells in 96-well plates. Subsequently, the cells are infected immediately with SARS-CoV-2 (MOI=0.01). Non-treated cells—with and without virus infection—serve as controls and contain the corresponding max. final DMSO concentration as well. Each data point is tested in triplicates. After 48 h treatment, the cells are either fixed and inspected by high content imaging or stained with resazurin cell viability staining.

In both cases the viability/presence of intact CACO-2 cells serve as measure to quantify the virus inhibition by the test compounds. In case of imaging quantification, the cells are fixed with 3% PFA in PBS, the 96-well plates are sealed and SARS-CoV-2 is inactivated by disinfection. The quantification is conducted by using an Operetta CLS (PerkinElmer)—in label-free mode just using the digital maximum phase contrast, and with cell nuclei staining using Hoechst 33258 (Sigma-Aldrich). For that purpose, cell images are acquired using a 10× objective, and 3×3 imaged field per 96-well are analyzed. In case of resazurin-based cell viability read-out, after 48 h cell treat-ment, medium is replaced by 50 μM resazurin in RPMI 1640, and the cells are incubated for 2 h. Subsequently, the conversion of resazurin to Resorufin by viable, metabolically active cells is measured using a Synergy 2 multiwell plate reader (BioTek, Bad Friedrichshall, Germany) with 540 nm excitation and 590 nm emission filter setting.

Results are normalized to the corresponding intra-plate non-treated controls, whereby without virus re-flected 100% cell viability or 0% viral cytotoxicity=100% inhibition of viral toxicity; with virus re-flected 0% cell viability or 100% viral cytotoxicity=0% inhibition of viral toxicity. Dose-response curves are analyzed by using GraphPad Prism resulting in IC50 values.

Example 4

In Vitro Viral Load Assay for Screening of Antiviral Compounds

An RT-qPCR-based viral load assay is used to screen the test items for anti-SARS-CoV-2 activity. In brief, test compounds are diluted to appropriate concentrations in MEM supplemented with 1% FBS (reduced FBS content)-10 μM (0.1% DMSO finally) for initial compound fast-screening and 0.02-50 μM (max. 0.5% DMSO finally) for IC50 analyses, respectively—and added to dense but still subconfluent CACO-2 cells in 96-well plates. Subsequently, the cells are infected immediately with SARS-CoV-2. Non-treated cells—with and without virus infection—serve as controls and contain the corresponding max. final DMSO concentration as well. Each data point is tested in triplicates. After 72 h treatment, cell supernatants are collected and centrifuged (2,000 rpm, 5 min) to remove cells and cell debris. Subsequently, viral RNAs are extracted from the cell supernatants by using a MagNA Pure 24 system (Roche, Mannheim, Germany). The RNA of SARS-CoV-2 is quantified using the TIB MOLBIOL LightMix Assay SARS-CoV-2 RdRP RT-qPCR assay kit with RNA Process Control PCR Kit (Roche), all according to the manufacturer's guidelines. PCR amplification is conducted by using a LightCycler 480 II (Roche). AACt values are taken as measures for SARS-CoV-2 viral replication. Dose-response curves for compound-mediated inhibition of the viral replication are analyzed by using GraphPad Prism resulting in IC50 values.

The examples and embodiments described herein are for illustrative purposes only and in some embodiments, various modifications or changes are to be included within the purview of disclosure and scope of the appended claims.

What is claimed is:

1. A compound having Formula V:

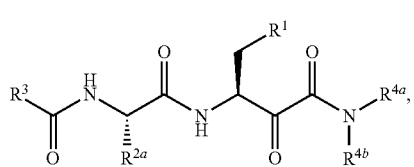

or a stereoisomer, tautomer, pharmaceutically acceptable salt, or solvate thereof, wherein:

$R^1$ is selected from the group consisting of:

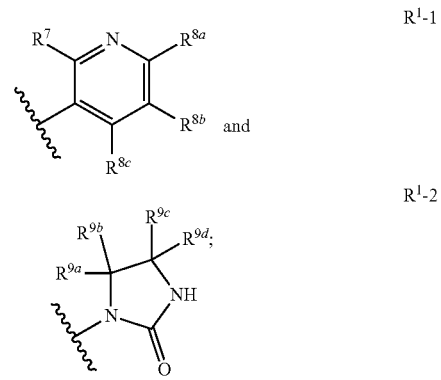

$R^{2a}$ is selected from the group consisting of $C_{1-6}$ alkyl, $C_{2-6}$ alkenyl, $C_{3-6}$ cycloalkyl, and —$C_{1-6}$ alkyl-$C_{3-6}$ cycloalkyl, wherein the $C_{1-6}$ alkyl, $C_{2-6}$ alkenyl, $C_{3-6}$ cycloalkyl, or —$C_{1-6}$ alkyl-$C_{3-6}$ cycloalkyl is independently optionally substituted with one, two, three, or four groups independently selected from the group consisting of halogen, $C_{1-6}$ alkyl, $C_{1-6}$ haloalkyl, —$OR^5$, and —$N(R^5)(R^6)$;

$R^3$ is selected from the group consisting of:

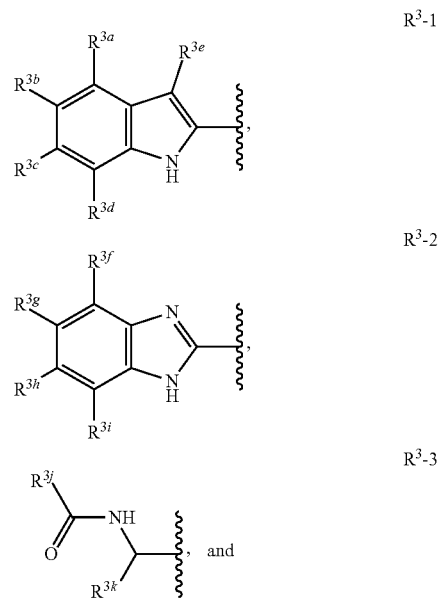

-continued

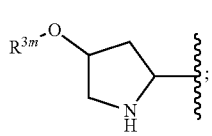
R³-4

R$^{3a}$, R$^{3b}$, R$^{3c}$, and R$^{3d}$ are independently selected from the group consisting of hydrogen, halogen, cyano, C$_{1-6}$ alkyl, C$_{1-6}$ haloalkyl, C$_{3-6}$ cycloalkyl, —OR$^5$, and —N(R$^5$)(R$^6$); or R$^{3a}$ and R$^{3b}$ taken together with the carbon atoms to which they are attached form a 5- or 6-membered heterocycloalkyl, wherein the 5- or 6-membered heterocycloalkyl is independently optionally substituted with one or two C$_{1-6}$ alkyl groups; and R$^{3c}$ and R$^{3d}$ are independently selected from the group consisting of hydrogen, halogen, cyano, C$_{1-6}$ alkyl, C$_{1-6}$ haloalkyl, C$_{3-6}$ cycloalkyl, —OR$^5$, and —N(R$^5$)(R$^6$); or R$^{3b}$ and R$^{3c}$ taken together with the carbon atoms to which they are attached form a 5- or 6-membered heterocycloalkyl, wherein the 5- or 6-membered heterocycloalkyl is independently optionally substituted with one or two C$_{1-6}$ alkyl groups; and R$^{3a}$ and R$^{3d}$ are independently selected from the group consisting of hydrogen, halogen, cyano, C$_{1-6}$ alkyl, C$_{1-6}$ haloalkyl, C$_{3-6}$ cycloalkyl, —OR$^5$, and —N(R$^5$)(R$^6$); or R$^{3c}$ and R$^{3d}$ taken together with the carbon atoms to which they are attached form a 5- or 6-membered heterocycloalkyl, wherein the 5- or 6-membered heterocycloalkyl is independently optionally substituted with one or two C$_{1-6}$ alkyl groups; and R$^{3a}$ and R$^{3b}$ are independently selected from the group consisting of hydrogen, halogen, cyano, C$_{1-6}$ alkyl, C$_{1-6}$ haloalkyl, C$_{3-6}$ cycloalkyl, —OR$^5$, and —N(R$^5$)(R$^6$);

R$^{3e}$ is selected from the group consisting of hydrogen and C$_{1-6}$ alkyl;

R$^{3f}$, R$^{3g}$, R$^{3h}$, and R$^{3i}$ are independently selected from the group consisting of hydrogen, halogen, cyano, C$_{1-6}$ alkyl, C$_{1-6}$ haloalkyl, C$_{3-6}$ cycloalkyl, —OR$^5$, and —N(R$^5$)(R$^6$); or R$^{3f}$ and R$^{3g}$ taken together with the carbon atoms to which they are attached form a 5- or 6-membered heterocycloalkyl, wherein the 5- or 6-membered heterocycloalkyl is independently optionally substituted with one or two C$_{1-6}$ alkyl groups; and R$^{3h}$ and R$^{3i}$ are independently selected from the group consisting of hydrogen, halogen, cyano, C$_{1-6}$ alkyl, C$_{1-6}$ haloalkyl, C$_{3-6}$ cycloalkyl, —OR$^5$, and —N(R$^5$)(R$^6$); or R$^{3g}$ and R$^{3h}$ taken together with the carbon atoms to which they are attached form a 5- or 6-membered heterocycloalkyl, wherein the 5- or 6-membered heterocycloalkyl is independently optionally substituted with one or two C$_{1-6}$ alkyl groups; and R$^{3f}$ and R$^{3i}$ are independently selected from the group consisting of hydrogen, halogen, cyano, C$_{1-6}$ alkyl, C$_{1-6}$ haloalkyl, C$_{3-6}$ cycloalkyl, —OR$^5$, and —N(R$^5$)(R$^6$); or R$^{3h}$ and R$^{3i}$ taken together with the carbon atoms to which they are attached form a 5- or 6-membered heterocycloalkyl, wherein the 5- or 6-membered heterocycloalkyl is independently optionally substituted with one or two C$_{1-6}$ alkyl groups; and R$^{3f}$ and R$^{3g}$ are independently selected from the group consisting of hydrogen, halogen, cyano, C$_{1-6}$ alkyl, C$_{1-6}$ haloalkyl, C$_{3-6}$ cycloalkyl, —OR$^5$, and —N(R$^5$)(R$^6$);

R$^{3j}$ is selected from the group consisting of C$_{1-6}$ alkyl and C$_{1-6}$ haloalkyl;

R$^{3k}$ is selected from the group consisting of C$_{1-6}$ alkyl and C$_{3-6}$ cycloalkyl;

R$^{3m}$ is selected from the group consisting of hydrogen and C$_{1-6}$ alkyl;

R$^{4a}$ is C$_{1-3}$ alkyl;

R$^{4b}$ is selected from the group consisting of hydrogen and C$_{1-3}$ alkyl; or R$^{4a}$ and R$^{4b}$ taken together with the nitrogen to which they are attached form a 3- to 8-membered heterocycloalkyl;

each R$^5$ is independently selected from the group consisting of hydrogen, C$_{1-6}$ alkyl, C$_{1-6}$ haloalkyl, C$_{2-6}$ alkenyl, C$_{2-6}$ alkynyl, C$_{3-6}$ cycloalkyl, C$_{2-9}$ heterocycloalkyl, C$_{6-10}$ aryl, and C$_1$-heteroaryl, wherein the C$_{1-6}$ alkyl, C$_{2-6}$ alkenyl, C$_{2-6}$ alkynyl, C$_{3-6}$ cycloalkyl, C$_{2-9}$ heterocycloalkyl, C$_{6-10}$ aryl, or C$_{1-9}$ heteroaryl are independently optionally substituted with one, two, or three groups independently selected from the group consisting of halogen, C$_{1-6}$ alkyl, C$_{1-6}$ haloalkyl, C$_{1-6}$ alkoxy, C$_{3-6}$ cycloalkyl, C$_{2-9}$ heterocycloalkyl, C$_{6-10}$ aryl, and C$_{1-9}$ heteroaryl;

each R$^6$ is independently selected from hydrogen, C$_{1-6}$ alkyl, and C$_{1-6}$ haloalkyl;

R$^7$ is selected from the group consisting of —OR$^{7a}$ and —NR$^{7b}$R$^{7c}$;

R$^{7a}$ is selected from the group consisting of hydrogen, C$_{1-6}$ alkyl, and C$_{3-6}$ cycloalkyl;

R$^{7b}$ and R$^{7c}$ are independently selected from the group consisting of hydrogen, C$_{1-6}$ alkyl, and C$_{3-6}$ cycloalkyl;

R$^{8a}$, R$^{8b}$, and R$^{8c}$ are independently selected from the group consisting of hydrogen, halogen, C$_{1-6}$ alkyl, C$_{1-6}$ haloalkyl, and —N(R$^5$)(R$^6$); and R$^{9a}$, R$^{9b}$, R$^{9c}$, and R$^{9d}$ are independently selected from the group consisting of hydrogen, halogen, C$_{1-6}$ alkyl, C$_{1-6}$ haloalkyl, —OR$^5$, and —N(R$^5$)(R$^6$).

2. The compound, stereoisomer, tautomer, pharmaceutically acceptable salt, or solvate thereof of claim 1, wherein R$^1$ is R$^1$-1 and R$^{8a}$, R$^{8b}$, and R$^{8c}$ are hydrogen.

3. The compound, stereoisomer, tautomer, pharmaceutically acceptable salt, or solvate thereof of claim 1, wherein R$^1$ is R$^1$-2 and R$^{9a}$, R$^{9b}$, R$^{9c}$, and Rod are hydrogen.

4. The compound, stereoisomer, tautomer, pharmaceutically acceptable salt, or solvate thereof of claim 1, wherein R$^3$ is R$^3$-1 and R$^3$-1 is selected from the group consisting of:

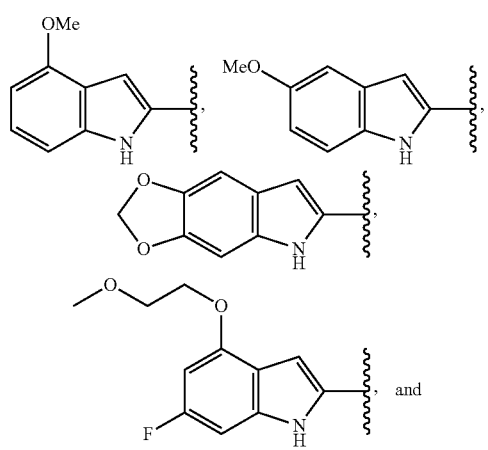

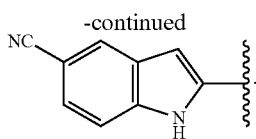

5. The compound, stereoisomer, tautomer, pharmaceutically acceptable salt, or solvate thereof of claim 1, wherein $R^3$ is $R^3$-2 and $R^3$-2 is selected from the group consisting of:

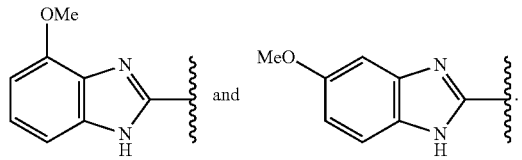 [SMILES: *c1nc2c(OC)cccc2[nH]1 ; *c1nc2cc(OC)ccc2[nH]1]

6. The compound, stereoisomer, tautomer, pharmaceutically acceptable salt, or solvate thereof of claim 1, wherein $R^3$ is $R^3$-3;
$R^3$-3 is:

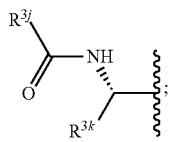

and
$R^{3j}$ is $C_{1-3}$haloalkyl.

7. The compound, stereoisomer, tautomer, pharmaceutically acceptable salt, or solvate thereof of claim 1, wherein $R^3$ is $R^3$-4 and $R^3$-4 is:

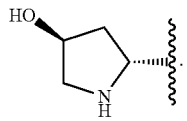

8. A pharmaceutical composition comprising a therapeutically effective amount of the compound, stereoisomer, tautomer, pharmaceutically acceptable salt, or solvate thereof of claim 1, and a pharmaceutically acceptable excipient.

9. A compound selected from the group consisting of:
N-((S)-1-(((S)-1-(2-hydroxypyridin-3-yl)-4-(methylamino)-3,4-dioxobutan-2-yl)amino)-4-methyl-1-oxopentan-2-yl)-4-methoxy-1H-indole-2-carboxamide;
4-methoxy-N-((S)-4-methyl-1-(((S)-4-(methylamino)-3,4-dioxo-1-(2-oxoimidazolidin-1-yl)butan-2-yl)amino)-1-oxopentan-2-yl)-1H-indole-2-carboxamide;
(S)-2-((S)-3,3-dimethyl-2-(2,2,2-trifluoroacetamido)butanamido)-4-methyl-N-((S)-4-(methylamino)-3,4-dioxo-1-(2-oxoimidazolidin-1-yl)butan-2-yl)pentanamide;
6-fluoro-N-((S)-1-(((S)-1-(2-hydroxypyridin-3-yl)-4-(methylamino)-3,4-dioxobutan-2-yl)amino)-4-methyl-1-oxopentan-2-yl)-4-(2-methoxyethoxy)-1H-indole-2-carboxamide;
(2R,4S)-4-hydroxy-N-((S)-4-methyl-1-(((S)-4-(methylamino)-3,4-dioxo-1-(2-oxoimidazolidin-1-yl)butan-2-yl)amino)-1-oxopentan-2-yl)pyrrolidine-2-carboxamide;
5-cyano-N-((S)-1-(((S)-1-(2-hydroxypyridin-3-yl)-4-(methylamino)-3,4-dioxobutan-2-yl)amino)-4-methyl-1-oxopentan-2-yl)-1H-indole-2-carboxamide;
N-((S)-1-(((S)-1-(2-hydroxypyridin-3-yl)-4-(methylamino)-3,4-dioxobutan-2-yl)amino)-4-methyl-1-oxopentan-2-yl)-5-methoxy-1H-benzo[d]imidazole-2-carboxamide;
(S)-2-((S)-3,3-dimethyl-2-(2,2,2-trifluoroacetamido)butanamido)-N-((S)-1-(2-hydroxypyridin-3-yl)-4-(methylamino)-3,4-dioxobutan-2-yl)-4-methylpentanamide;
4-methoxy-N-((S)-4-methyl-1-(((S)-4-(methylamino)-3,4-dioxo-1-(2-oxoimidazolidin-1-yl)butan-2-yl)amino)-1-oxopentan-2-yl)-1H-benzo[d]imidazole-2-carboxamide;
(S)-2-((S)-3,3-dimethyl-2-(2,2,2-trifluoroacetamido)butanamido)-4-methyl-N-((S)-4-(methylamino)-3,4-dioxo-1-(2-oxoimidazolidin-1-yl)butan-2-yl)pentanamide;
N-((S)-1-(((S)-4-(aziridin-1-yl)-1-(2-hydroxypyridin-3-yl)-3,4-dioxobutan-2-yl)amino)-4-methyl-1-oxopentan-2-yl)-4-methoxy-1H-indole-2-carboxamide;
N-((S)-1-(((S)-1-(2-hydroxypyridin-3-yl)-4-(methylamino)-3,4-dioxobutan-2-yl)amino)-4-methyl-1-oxopentan-2-yl)-5H-[1,3]dioxolo[4,5-f]indole-6-carboxamide;
4-methoxy-N-((S)-1-(((S)-1-(2-methoxypyridin-3-yl)-4-(methylamino)-3,4-dioxobutan-2-yl)amino)-4-methyl-1-oxopentan-2-yl)-1H-indole-2-carboxamide;
N-((S)-1-(((S)-1-(2-aminopyridin-3-yl)-4-(methylamino)-3,4-dioxobutan-2-yl)amino)-4-methyl-1-oxopentan-2-yl)-4-methoxy-1H-indole-2-carboxamide;
N-((S)-1-(((S)-1-(2-hydroxypyridin-3-yl)-4-(methylamino)-3,4-dioxobutan-2-yl)amino)-4-methyl-1-oxopentan-2-yl)-5-methoxy-1H-indole-2-carboxamide;
(1R,2S,5S)-3-((S)-3,3-dimethyl-2-(2,2,2-trifluoroacetamido)butanoyl)-N-((S)-1-(2-hydroxypyridin-3-yl)-4-(methylamino)-3,4-dioxobutan-2-yl)-6,6-dimethyl-3-azabicyclo[3.1.0]hexane-2-carboxamide; and
(1R,2S,5S)-3-((S)-3,3-dimethyl-2-(2,2,2-trifluoroacetamido)butanoyl)-6,6-dimethyl-N-((S)-4-(methylamino)-3,4-dioxo-1-(2-oxoimidazolidin-1-yl)butan-2-yl)-3-azabicyclo[3.1.0]hexane-2-carboxamide,
or a stereoisomer, tautomer, pharmaceutically acceptable salt, or solvate thereof.

10. A method of treating coronavirus disease 2019 (COVID-19) in an individual in need thereof comprising administering to the individual a therapeutically effective amount of:
N-((S)-1-(((S)-1-(2-hydroxypyridin-3-yl)-4-(methylamino)-3,4-dioxobutan-2-yl)amino)-4-methyl-1-oxopentan-2-yl)-4-methoxy-1H-indole-2-carboxamide, or a stereoisomer, tautomer, pharmaceutically acceptable salt, or solvate thereof; or
4-methoxy-N-((S)-4-methyl-1-(((S)-4-(methylamino)-3,4-dioxo-1-(2-oxoimidazolidin-1-yl)butan-2-yl)amino)-1-oxopentan-2-yl)-1H-indole-2-carboxamide, or a stereoisomer, tautomer, pharmaceutically acceptable salt, or solvate thereof.

* * * * *